US011213337B2

(12) United States Patent
Rossney et al.

(10) Patent No.: US 11,213,337 B2
(45) Date of Patent: Jan. 4, 2022

(54) SYSTEMS AND METHODS FOR INTRAMEDULLARY NAIL IMPLANTATION

(71) Applicant: GLOBUS MEDICAL, INC., Audubon, PA (US)

(72) Inventors: Mark Rossney, Downingtown, PA (US); David J. Rowe, Parkesburg, PA (US); David R. Jansen, Glenmoore, PA (US)

(73) Assignee: Globus Medical, Inc., Audubon, PA (US)

( * ) Notice: Subject to any disclaimer, the term of this patent is extended or adjusted under 35 U.S.C. 154(b) by 134 days.

(21) Appl. No.: 16/580,174

(22) Filed: Sep. 24, 2019

(65) Prior Publication Data
US 2020/0015875 A1    Jan. 16, 2020

Related U.S. Application Data

(63) Continuation of application No. 15/636,806, filed on Jun. 29, 2017, now Pat. No. 10,463,416, which is a (Continued)

(51) Int. Cl.
A61B 17/72 (2006.01)
A61B 17/92 (2006.01)
(Continued)

(52) U.S. Cl.
CPC ........ *A61B 17/921* (2013.01); *A61B 17/1721* (2013.01); *A61B 17/1725* (2013.01);
(Continued)

(58) Field of Classification Search
CPC .......................................... A61B 17/72–7291
See application file for complete search history.

(56) References Cited

U.S. PATENT DOCUMENTS 4,978,349 A * 12/1990 Frigg ................. A61B 17/1721
606/62
5,034,013 A    7/1991 Kyle et al.
(Continued)

FOREIGN PATENT DOCUMENTS

CN    201524132 U    7/2010
DE    4445692 A1    5/1996
(Continued)

*Primary Examiner* — Eduardo C Robert
*Assistant Examiner* — Steven J Cotroneo

(57) ABSTRACT

Intramedullary nails, systems, and methods. The intramedullary nail may include a generally elongate body extending from a first, distal end to a second, proximal end. The distal end may include one or more openings configured to receive one or more bone anchors that extend transversely through the distal end intramedullary nail, and thereby configured to secure the distal end of the nail. The proximal end may also include one or more openings configured to receive one or more bone anchors that extend transversely through the proximal end of the intramedullary nail, and thereby configured to secure the proximal end of the nail. In some embodiments, the proximal end may further include a cross-locking feature, which includes a second bone anchor that interlocks with a first bone anchor, for example, for enhanced bone purchase and bony fixation.

17 Claims, 20 Drawing Sheets

Related U.S. Application Data continuation-in-part of application No. 15/272,850, filed on Sep. 22, 2016, now Pat. No. 10,299,847.

(51) Int. Cl.

| | | |
|---|---|---|
| *A61B 17/74* | (2006.01) | |
| *A61B 17/17* | (2006.01) | |
| *A61B 17/88* | (2006.01) | |
| *A61B 17/16* | (2006.01) | |
| *A61B 17/90* | (2006.01) | |

(52) U.S. Cl.
CPC ............ *A61B 17/72* (2013.01); *A61B 17/725* (2013.01); *A61B 17/7233* (2013.01); *A61B 17/7275* (2013.01); *A61B 17/7283* (2013.01); *A61B 17/744* (2013.01); *A61B 17/8872* (2013.01); *A61B 17/1668* (2013.01); *A61B 17/1742* (2013.01); *A61B 17/8875* (2013.01); *A61B 17/90* (2021.08)

(56) References Cited

U.S. PATENT DOCUMENTS

| | | | |
|---|---|---|---|
| 5,429,640 A * | 7/1995 | Shuler | A61B 17/7233 606/62 |
| 5,741,256 A | 4/1998 | Bresina | |
| 6,221,074 B1 * | 4/2001 | Cole | A61B 17/72 606/60 |
| 6,514,253 B1 | 2/2003 | Yao | |
| 7,001,388 B2 * | 2/2006 | Orbay | A61B 17/8061 606/286 |
| 7,918,853 B2 * | 4/2011 | Watanabe | A61B 17/1684 606/64 |
| 8,591,513 B2 * | 11/2013 | Overes | A61B 17/80 606/64 |
| 10,022,135 B2 | 7/2018 | O'Reilly et al. | |
| 2002/0029041 A1 | 3/2002 | Hover et al. | |
| 2003/0074078 A1 | 4/2003 | Doubler et al. | |
| 2006/0030859 A1 | 2/2006 | Gotfried | |
| 2006/0064106 A1 | 3/2006 | Fernandez | |
| 2006/0200160 A1 | 9/2006 | Border et al. | |
| 2008/0281331 A1 | 11/2008 | Fritzinger et al. | |
| 2009/0200160 A1 | 8/2009 | Abe et al. | |
| 2010/0063503 A1 | 3/2010 | Dell'Oca | |
| 2011/0054474 A1 | 3/2011 | Metzinger et al. | |
| 2011/0077693 A1 | 3/2011 | Yu | |
| 2011/0282398 A1 * | 11/2011 | Overes | A61B 17/861 606/304 |
| 2013/0317502 A1 * | 11/2013 | Overes | A61B 17/746 606/66 |
| 2014/0214045 A1 | 7/2014 | Felder et al. | |
| 2015/0038967 A1 * | 2/2015 | Khong | A61B 17/72 606/64 |
| 2015/0038968 A1 | 2/2015 | Vega et al. | |
| 2016/0089189 A1 | 3/2016 | Buscaglia et al. | |
| 2018/0078292 A1 | 3/2018 | Hedgeland et al. | |
| 2018/0078294 A1 | 3/2018 | Hedgeland et al. | |
| 2018/0250040 A1 * | 9/2018 | Menci | A61B 17/744 |

FOREIGN PATENT DOCUMENTS

| | | |
|---|---|---|
| EP | 0321170 A1 | 6/1989 |
| EP | 0441577 A2 | 8/1991 |
| EP | 1759643 A1 | 3/2007 |
| EP | 2606836 A1 | 6/2013 |
| JP | 200150765 A | 6/2001 |
| JP | 2008514296 A | 5/2008 |
| JP | 2009-112594 A | 5/2009 |
| JP | 2009-534106 A | 9/2009 |
| JP | 2009-537106 A | 9/2009 |
| JP | 2011-500215 A | 1/2011 |
| JP | 2011-206125 A | 10/2011 |
| JP | 2012147948 A | 8/2012 |
| JP | 2013-502992 A | 1/2013 |
| JP | 2016-504961 A | 2/2016 |
| JP | 2018149273 A | 9/2018 |
| WO | 9415556 A1 | 7/1994 |
| WO | 2010053628 A1 | 5/2010 |
| WO | 2013092402 A1 | 6/2013 |
| WO | 20161511611 A1 | 9/2016 |
| WO | 2018091515 A1 | 5/2018 |

* cited by examiner

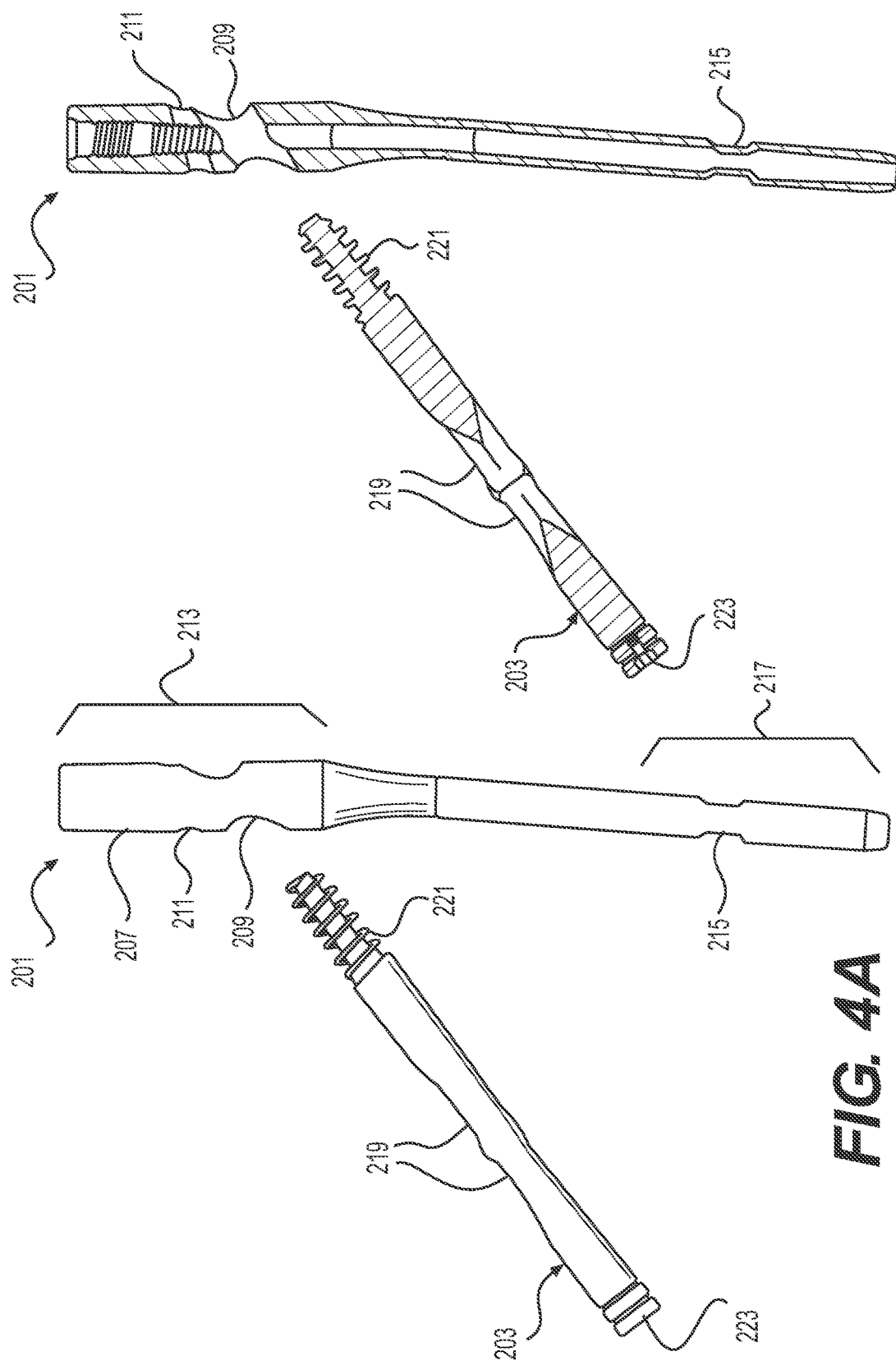

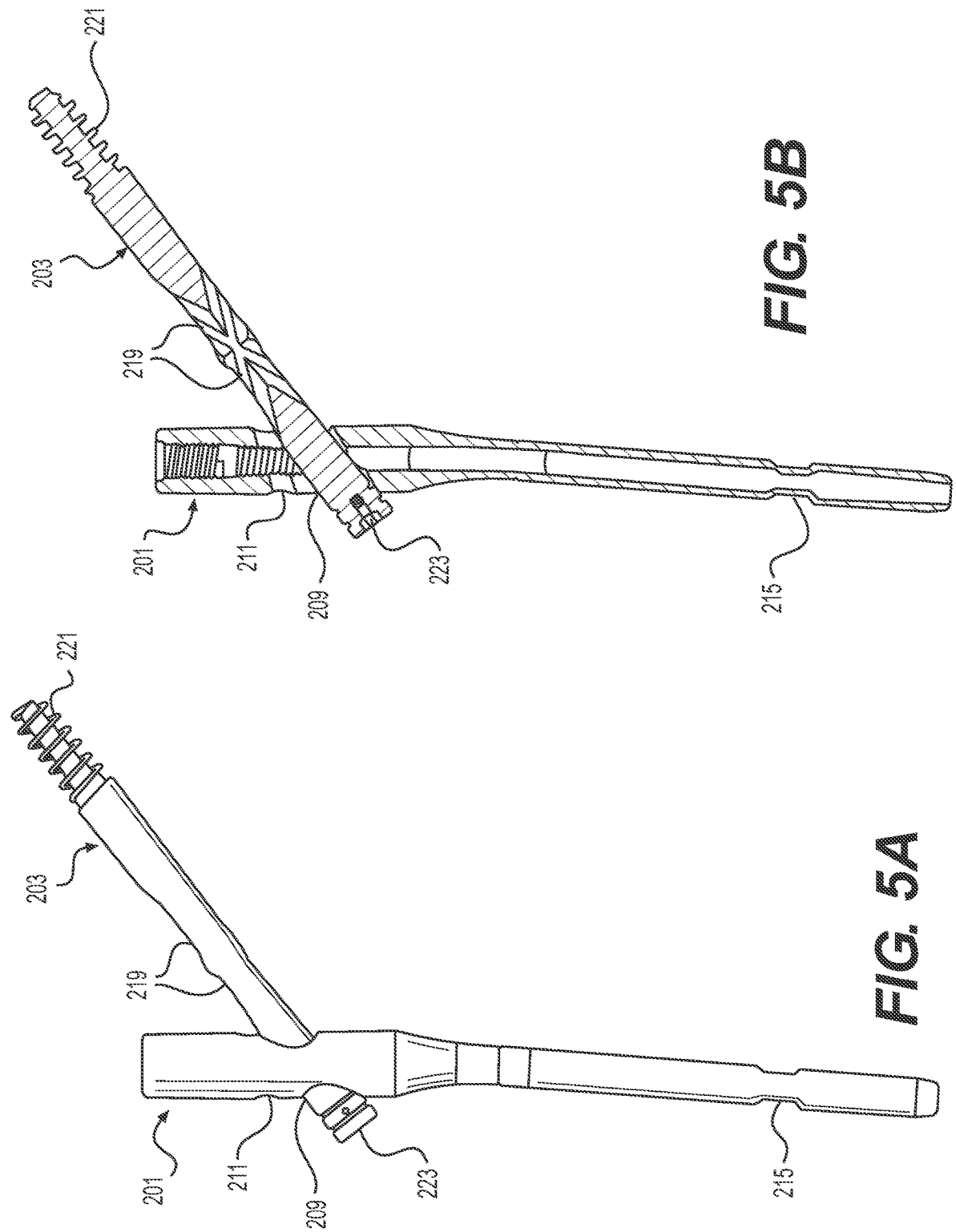

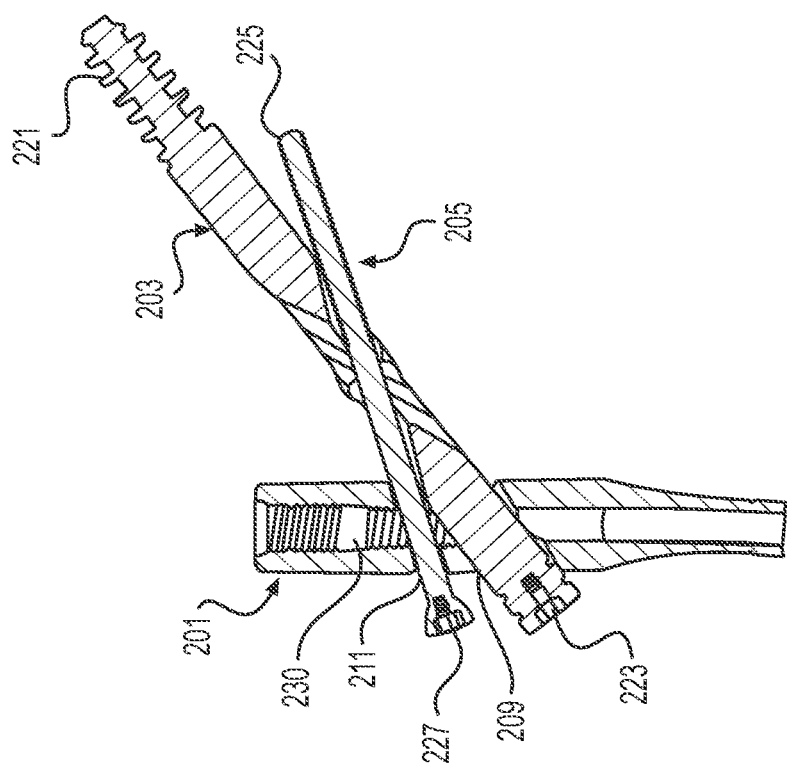
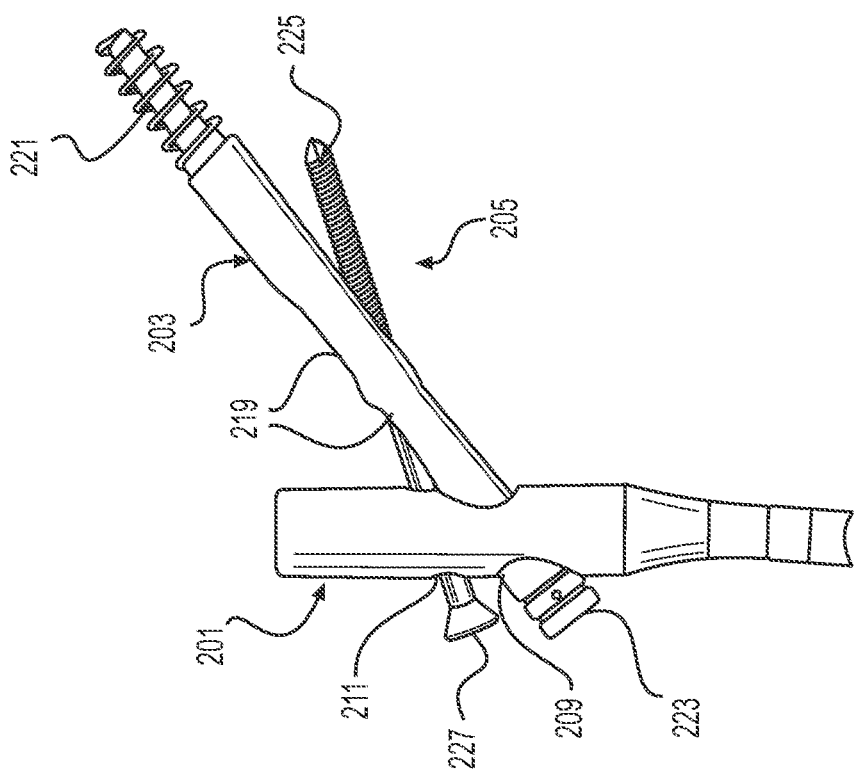
FIG. 7B
FIG. 7A

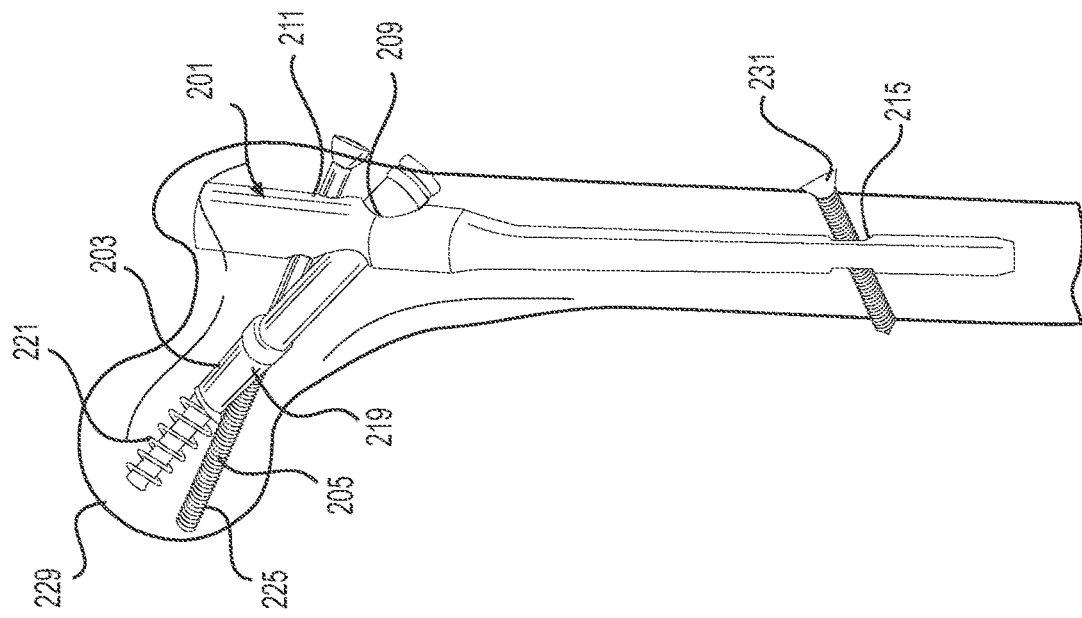
*FIG. 8C*
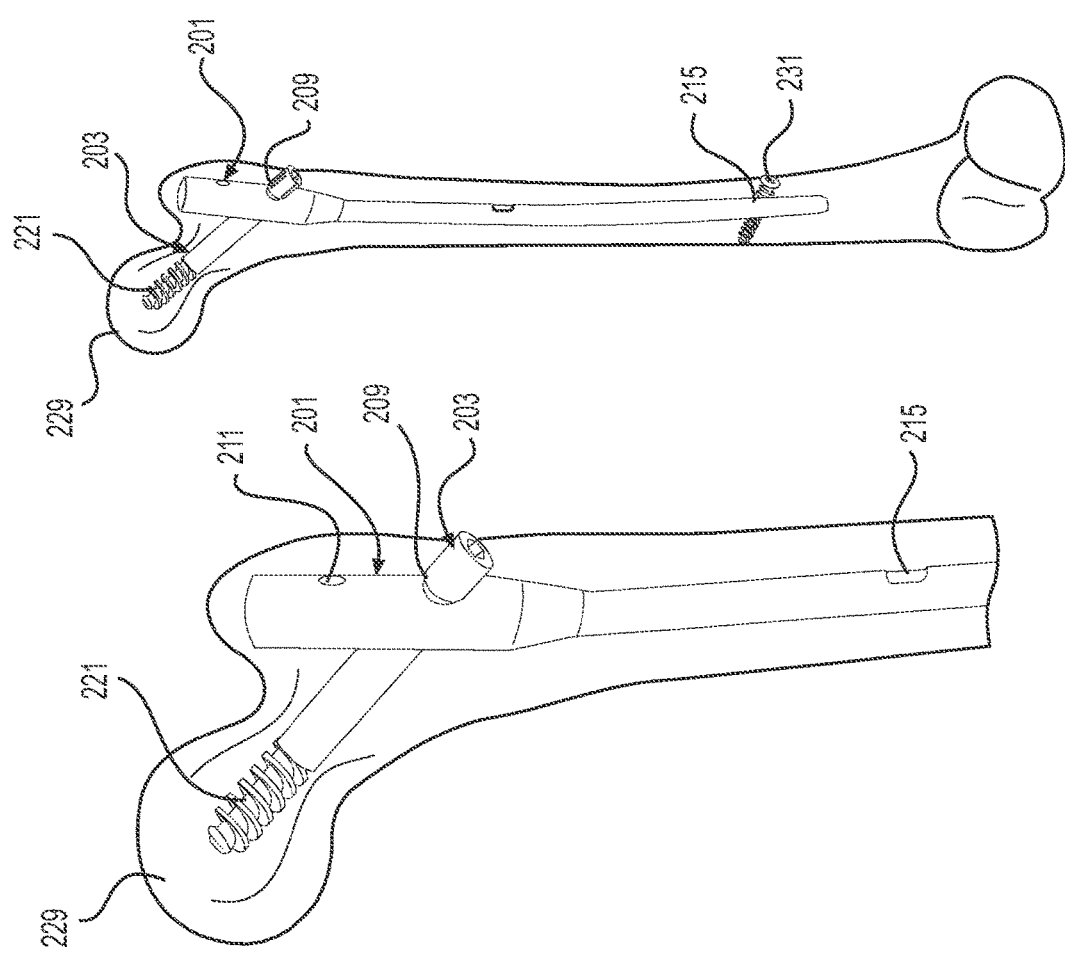
*FIG. 8B*
*FIG. 8A*

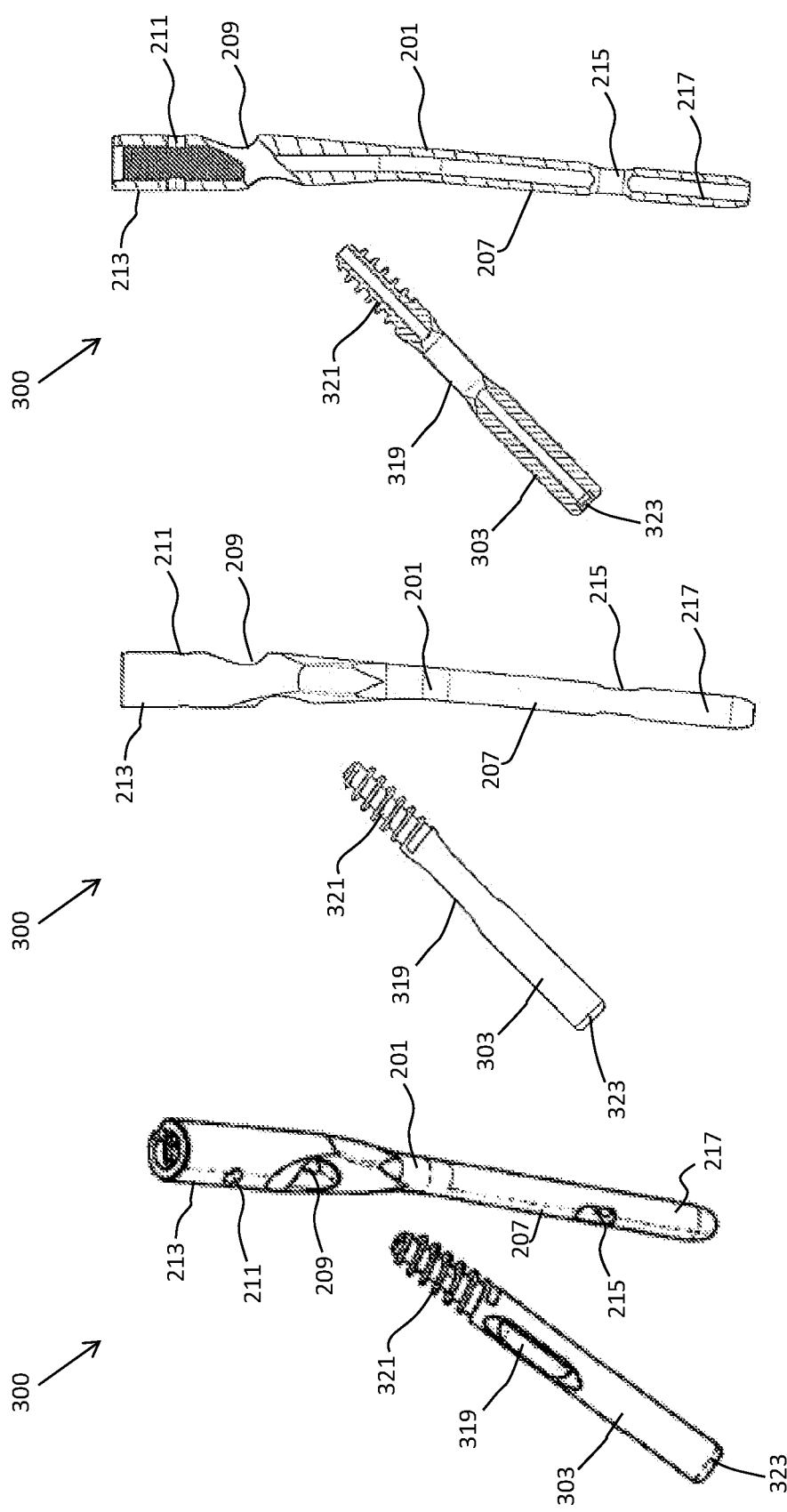

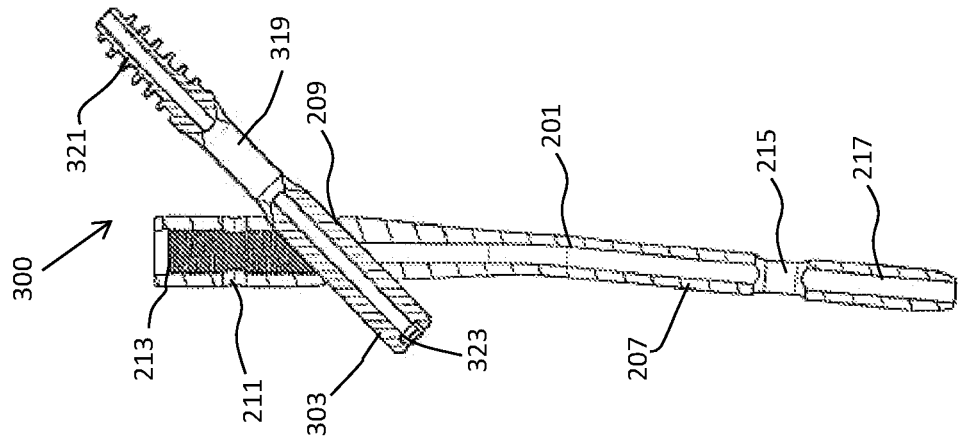
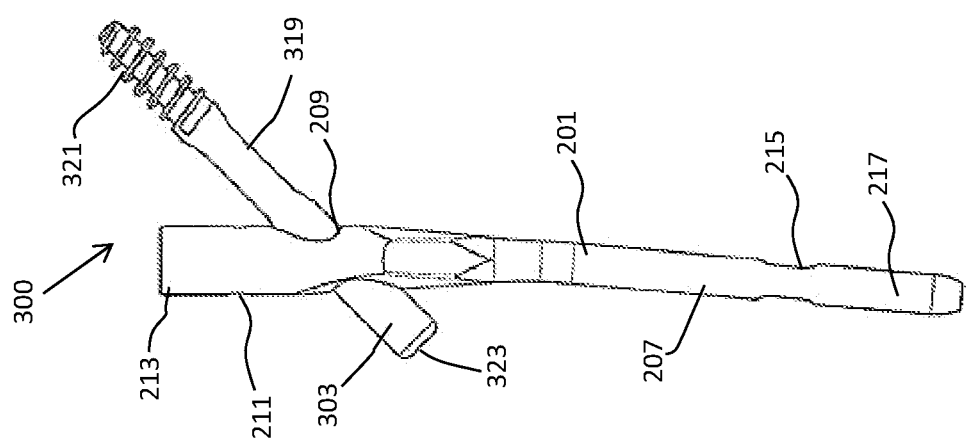
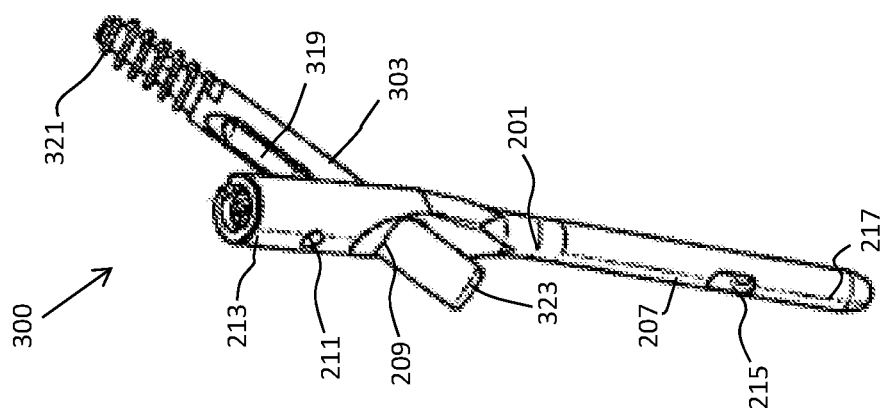

SYSTEMS AND METHODS FOR INTRAMEDULLARY NAIL IMPLANTATION

CROSS-REFERENCE TO RELATED APPLICATION

This application is a continuation of U.S. patent application Ser. No. 15/636,806, filed on Jun. 29, 2017 (published as U.S. Pat. Pub. No. 2018-0078290), which is a continuation-in-part of U.S. patent application Ser. No. 15/272,850, filed Sep. 22, 2016 (now U.S. Pat. No. 10,299,847), all of which are incorporated by reference herein in their entireties for all purposes.

TECHNICAL FIELD

The present technology is generally related to intramedullary nail implantation for treatment of bone fractures. In particular, several embodiments are directed to systems and methods for implanting an intramedullary nail for immobilizing bone fractures.

BACKGROUND

The significant long bones of the extremities are the humerus, radius and ulna of the upper extremity and the femur and tibia of the lower extremity. Following an injury to the long bone, and in particular, injuries resulting in one or more fractures of the long bone, one or more fixation devices may be used to immobilize the fracture fragments and stabilize the long bone. Bone fractures can be treated with screws or other fixation devices inserted into or through the bone to stabilize it once the fractured portions have been brought into proper alignment. Femoral neck fixation, for example, can be used to treat hip fractures by inserting an intramedullary nail into the medullary cavity of the fractured femur followed by insertion of a fixation screw into the femoral neck/head at an angle relative to the intramedullary nail. Similarly, other long bone fractures can be treated by inserting an intramedullary nail into the intramedullary canal of the bone and providing the appropriate proximal and/or distal fixation. Traditional intramedullary devices may suffer from a number of disadvantages, however. For example, they may be susceptible to implant failure and difficulty in alignment of the fixation screw with respect to the intramedullary nail. Accordingly, there is a need for improved systems and methods for intramedullary nail implantation.

SUMMARY

Intramedullary nails, systems, insertion tools, and method of treatment are provided. The intramedullary nails may be suitable for implanting within a medullary canal of a fractured long bone and subsequently providing proximal fixation and/or distal fixation, for example, with one or more anchors, fasteners, fixation screws, or the like. Suitable long bones may include the humerus, radius, ulna, femur, tibia, or the like. Although generally described with reference to the femur, it will be appreciated that the intramedullary nail and system may be adapted for use with any long bone.

According to one aspect, an intramedullary nail is provided. The intramedullary nail may comprise a generally elongate body extending from a first, distal end to a second, proximal end. The distal end may include one or more openings configured to receive one or more bone anchors or fasteners that extend transversely through the distal end intramedullary nail, and thereby configured to secure the distal end of the nail. The proximal end may also include one or more openings configured to receive one or more bone anchors or fasteners that extend transversely through the proximal end of the intramedullary nail, and thereby configured to secure the proximal end of the nail.

In one aspect, a system for inserting an intramedullary nail into a bone is provided. The system includes an intramedullary nail with an opening or aperture formed therein. An insertion tool includes can temporarily engage with an end of the intramedullary nail during implantation, and release from the nail once the procedure is complete. A receiving feature for a guide sheath (e.g., a hole, recess, etc.) is disposed in the handle portion and can receive a guide sheath therethrough. The receiving feature defines an axis such that, when the intramedullary nail is coupled to the coupling portion, a guide sheath inserted through the receiving feature substantially aligns with the aperture in the intramedullary nail. A first retention member is disposed in the insertion tool adjacent to the guide sheath receiving feature. The first retention member can interact with a second retention member on the guide sheath to form a ratchet-like mechanism that restrict movement of the guide sheath with respect to the receiving feature. A retention release mechanism can be located on a lower portion (e.g., a bottom surface) of the insertion tool. A guide wire receptacle (e.g., a hole, recess, etc.) can receives a guide wire therethrough and is positioned such that, when the intramedullary nail is coupled to the coupling portion, a guide wire inserted through the receiving feature runs along an axis adjacent to the side surface of the intramedullary nail.

In another aspect, a method for inserting an intramedullary nail into a patient is provided. The method includes inserting a nail into a medullary canal of a patient along a first axis. For insertion, the nail is coupled at its proximal end to an insertion tool. A guide wire is inserted through a guide wire hole in the insertion tool along a second axis such that the guide wire runs nearby or adjacent to a side surface of the nail. A screw or other bone fixation device is inserted through receptacle (e.g., a hole, recess, or other suitable structure) formed in the insertion tool such that the screw passes through an aperture formed in the nail.

In accordance with another aspect, an implant is provided. The implant includes an intramedullary nail that is elongated along a first axis. First and second openings or apertures are disposed in a proximal portion of the nail. The first aperture defines a second axis transverse to the first axis, and the second aperture defines a third axis transverse to the first axis. The third axis intersects with the second axis at a point spaced apart from the nail. In some embodiments, the first screw can be inserted through the first aperture along the second axis and a second screw can be inserted through the second aperture along the third axis. The second screw can be at least partially inserted through a slot in the first screw such that the two screws interlock. The second screw can be shorter than the first screw but long enough that at least a threaded distal tip extends beyond the slot in the first screw to provide some purchase in the bone.

In accordance with another embodiment, an implant includes an intramedullary nail, a first fixation device, and a second fixation device. The intramedullary nail has an elongate body extending from a proximal portion to a distal portion where a portion of the elongate body extends along a first axis. A first aperture is formed in the proximal portion. The first aperture defines a second axis transverse to the first axis. A second aperture is formed in the proximal portion. The second aperture is spaced apart from the first aperture. The second aperture defines a third axis transverse to the first axis. The third axis intersects with the second axis at a point spaced apart from the body. The first fixation device is positionable through the first aperture in the nail. The first fixation device has an elongate slot extending therethrough. The second fixation device is positionable through the second aperture in the nail, and the second fixation device is positionable through the elongate slot in the first fixation device.

Also provided are kits including intramedullary nails of varying shapes and sizes, bone anchors, fasteners, insertion tools, and components for installing the same.

BRIEF DESCRIPTION OF THE DRAWINGS

A more complete understanding of the present invention, and the attendant advantages and features thereof, will be more readily understood by reference to the following detailed description when considered in conjunction with the accompanying drawings wherein:

FIGS. 4A-4D illustrate various views of an intramedullary nail and a first fixation device.

FIGS. 5A-5D illustrate various views of the first fixation device inserted through the intramedullary nail.

FIGS. 7A-7D illustrate various views of the second anchor inserted through the intramedullary nail and the first fixation device.

FIGS. 8A-8C illustrate steps of implanting an intramedullary nail with interlocking fixation devices into a fractured femur.

FIGS. 9A-9C depict various views of an intramedullary nail and a first fixation device according to another embodiment.

FIGS. 10A-10C illustrate various views of the first fixation device inserted through the intramedullary nail.

DETAILED DESCRIPTION

Figure 1A:
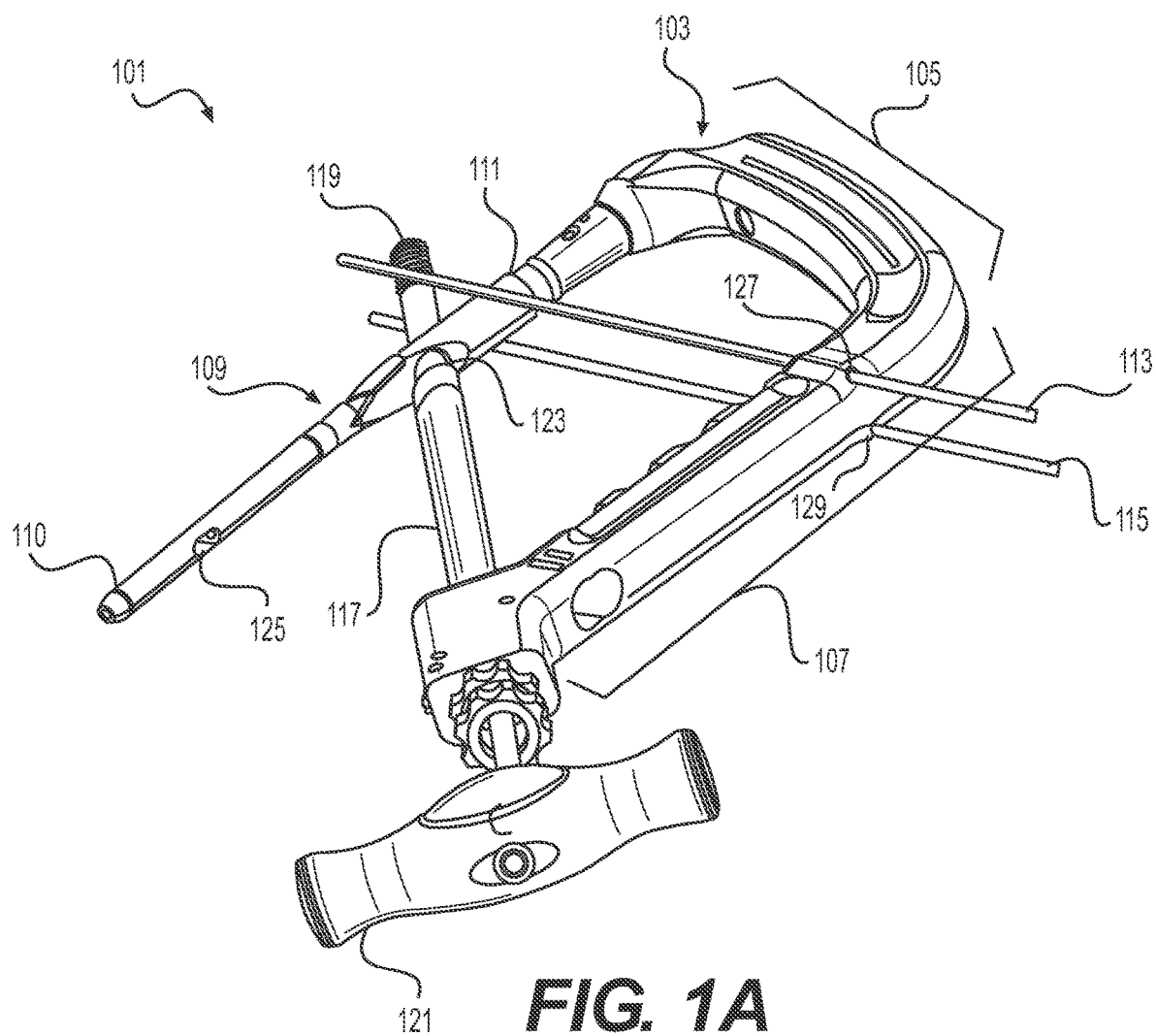
FIGS. 1A and 1B illustrate a system for implanting an intramedullary nail.

Intramedullary nails, systems, insertion tools, and method of treatment are provided. The intramedullary nails may be suitable for implantation within the intramedullary canal of a fractured long bone and subsequently providing proximal fixation and/or distal fixation, for example, with one or more anchors, fasteners, fixation screws, or the like. Suitable long bones may include the humerus, radius, ulna, femur, tibia, or the like. Although further described with reference to hip fractures of the femur, it will be appreciated that the intramedullary nail and system may be adapted for use with any long bone.

In conventional hip fracture fixation techniques, there are four main failure modes: axial cutout, cephalad cutout, proximal fragment rotation, and nonunion. "Cutout" is the term for hip screw subsidence into the articular surface of the hip. Cutout can occur in either a cephalad (toward the head) or axial direction (along the axis of the hip screw). Axial cutout is the result of an implant with a small axial profile that provides little resistance to axial translation. Axial cutout can be addressed by the "controlled collapse" features on certain modern hip fracture nails; the hip screw is allowed to translate through the nail, even after the set screw is locked in place. Cephalad cutout is the radial translation of the nail which is the result of a narrow implant that "windshield wipers" through the weak cancellous bone in the hip. Proximal fragment rotation is the result of a circular profile hip screw that acts as a fulcrum to the proximal hip fragment. Fracture nonunion is the result of biologic or mechanical factors that are incompatible with the bone healing process. Biologic factors of the patient are not controllable by the implant. Mechanical factors are those that typically allow fixation that is too rigid or too flexible. Nonunion is usually the precursor to one of the other three failure modes. Occasionally, nonunion will cause the nail to break in fatigue before the bone fails.

The intramedullary nails and systems described herein may address one or more of these failure modes. In some embodiment, the intramedullary nail includes proximal and distal locking, for example, to prevent cutout. In other embodiments, the intramedullary nail may include proximal locking including two interlocking fixation devices (e.g., screws), for example, by providing converging and diverging purchase, along with bony fixation in the calcar of the femur, which is the strongest portion of the hip bone. Accordingly, the risk of failure due to cutout and/or rotation can be reduced.

Additionally, some intramedullary nail implantation systems fail to adequately address the problems of fragment rotation during implantation. Rotation occurs when fragments of the bone rotate about the axis of the screw during the implantation procedure. Conventional anti-rotation technologies require the use of additional instruments or are limited to a single wire placement. In some embodiments, an insertion tool is directly coupled to the intramedullary nail and additional instruments are not needed for the placement of an anti-rotation guide wire and allow the user to place one or more guide wires anterior and/or posterior to the nail. These guide wires can be positioned to prevent the distal fragments of the femoral head and neck from rotating about the axis of the anchor during the procedure.

Some systems may be susceptible to backout during the implantation procedure. Backout occurs when the guide sheath used to insert the screw through the intramedullary nail moves proximally away from the bone. Conventional systems either have no features to prevent backout or else provide backout prevention measures that obstruct the normal positioning of the hands during the procedure, resulting in the risk of releasing the guide sheaths and dropping them to the floor. Ratchets on the insertion tool may have the release button facing towards the grip portion on the insertion tool and may present the danger of the user's hand slipping and inadvertently pressing the button. Accidentally pressing the button could result in releasing the sheath and causing the sheath to fall on the floor. In some embodiments, a backout prevention system (e.g., a ratchet system) may be disposed on the lower end of the insertion tool, which allows a user to have a hand placed on the grip of the insertion tool without the risk of inadvertently pressing the ratchet release button.

Further specific details of several embodiments of the present technology are described below with reference to FIGS. 1A-8C. Although many of the embodiments are described below with respect to devices, systems, and methods for implantation of intramedullary nails, other embodiments are within the scope of the present technology. Additionally, other embodiments of the present technology can have different configurations, components, and/or procedures than those described herein. For example, other embodiments can include additional elements and features beyond those described herein, or other embodiments may not include several of the elements and features shown and described herein.

For ease of reference, throughout this disclosure identical reference numbers are used to identify similar or analogous components or features, but the use of the same reference number does not imply that the parts should be construed to be identical. Indeed, in many examples described herein, the identically numbered parts are distinct in structure and/or function.

Intramedullary Nail Implants and Systems

Figure 3A:
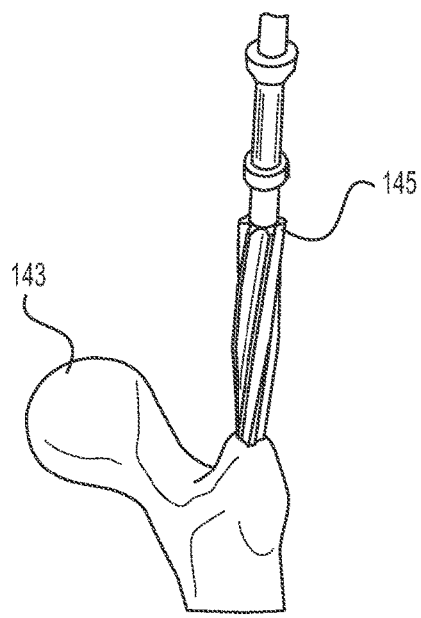
FIGS. 3A-3F illustrate steps of implanting an intramedullary nail into a fractured femur.
Figure 3B:
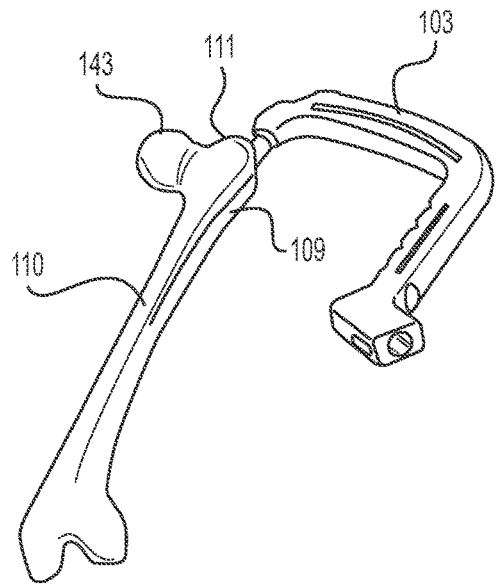
Figure 3C:
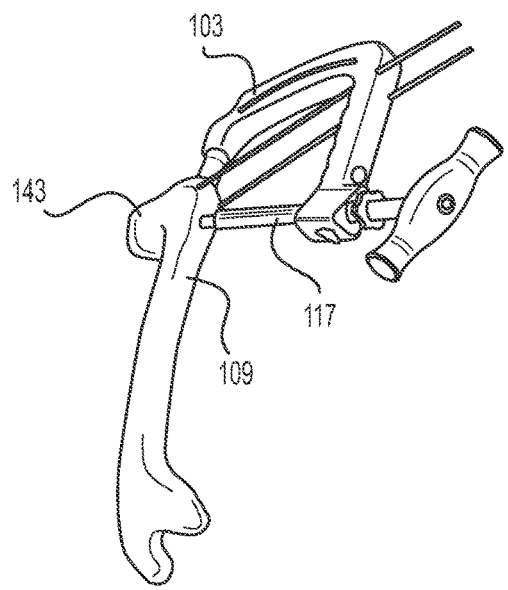
Figure 3D:
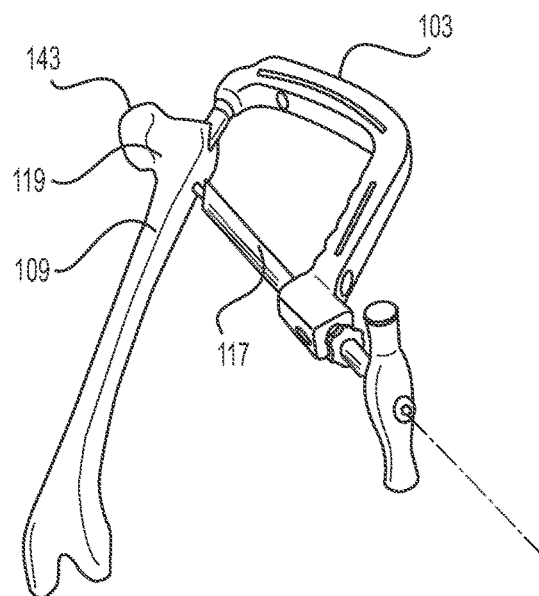
Figure 3E:
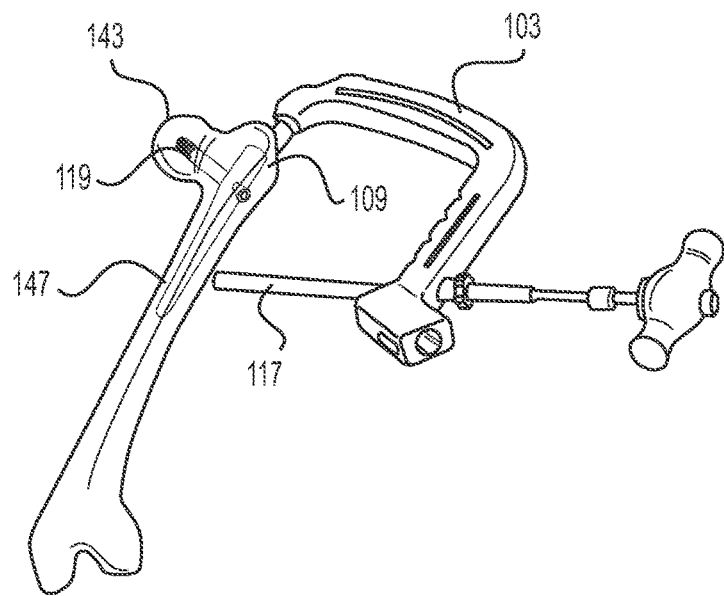
Figure 3F:
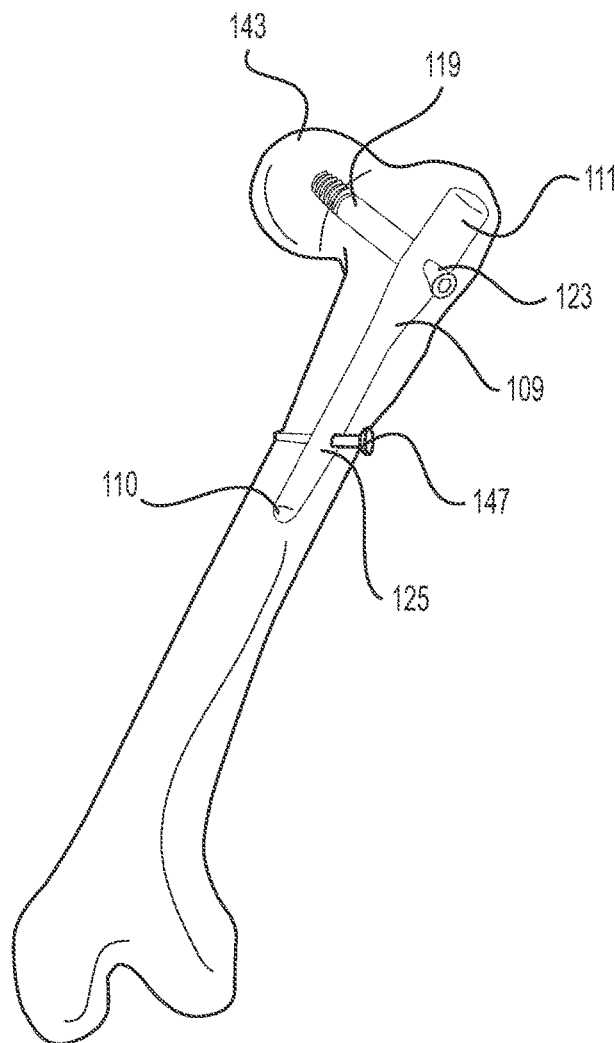
Figure 4D:
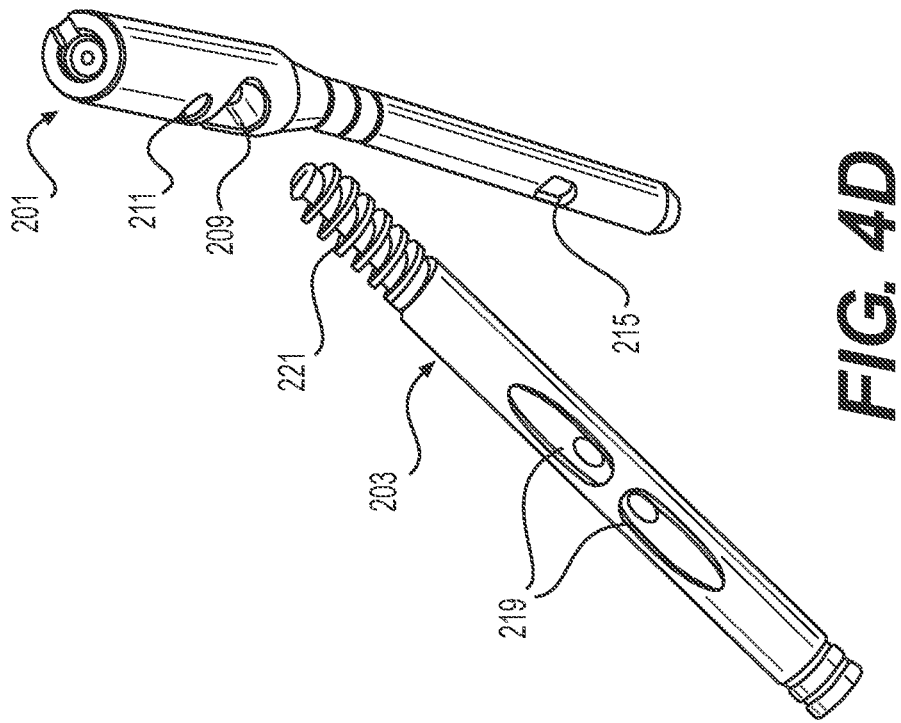
Figure 4C:
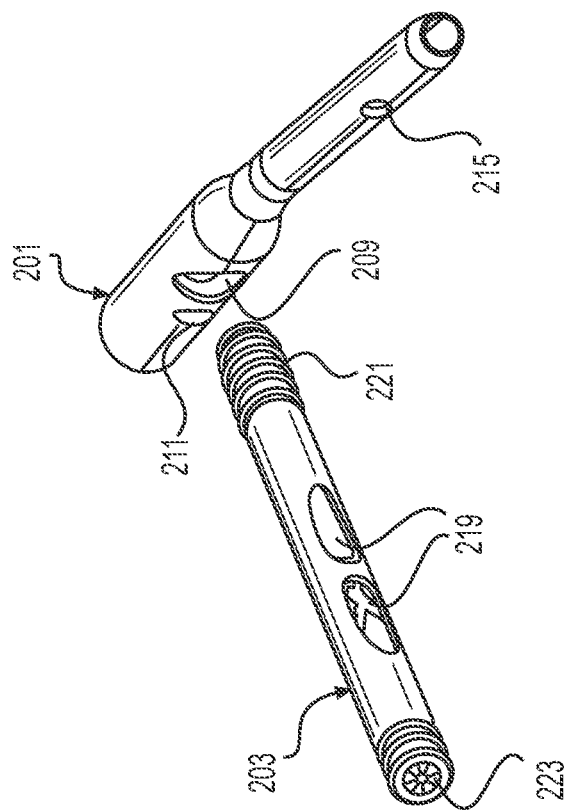
Figure 5D:
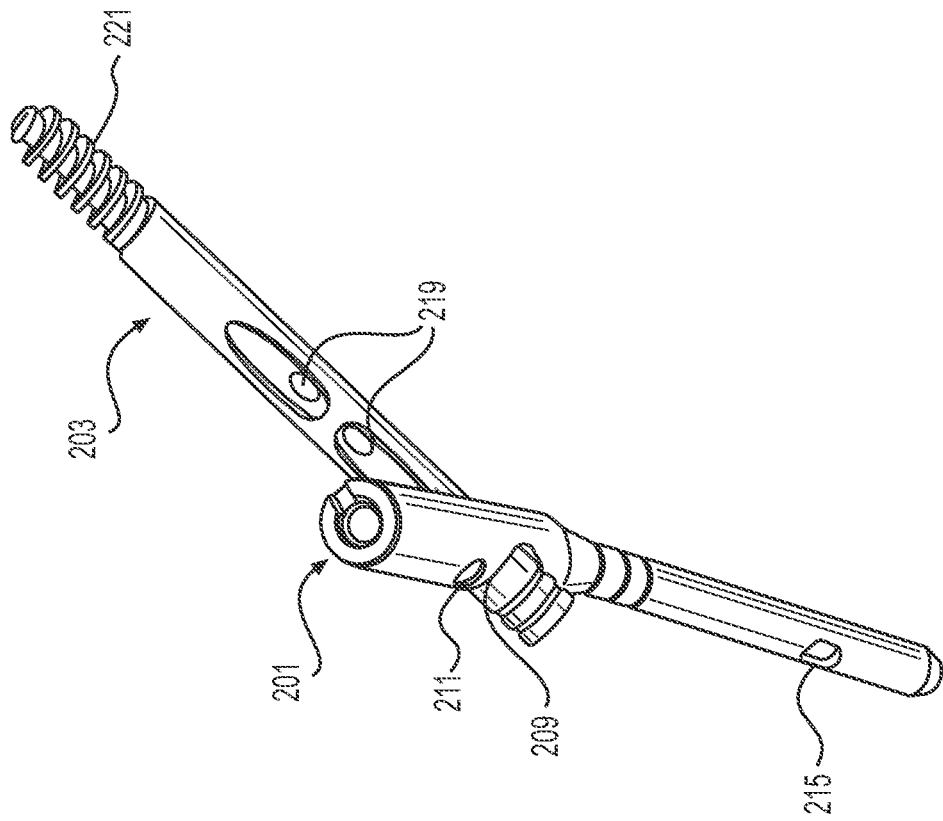
Figure 5C:
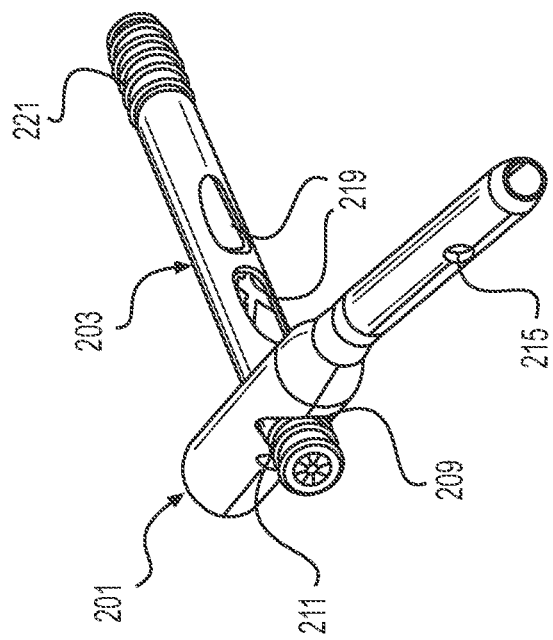
Figures 6A, 6B:
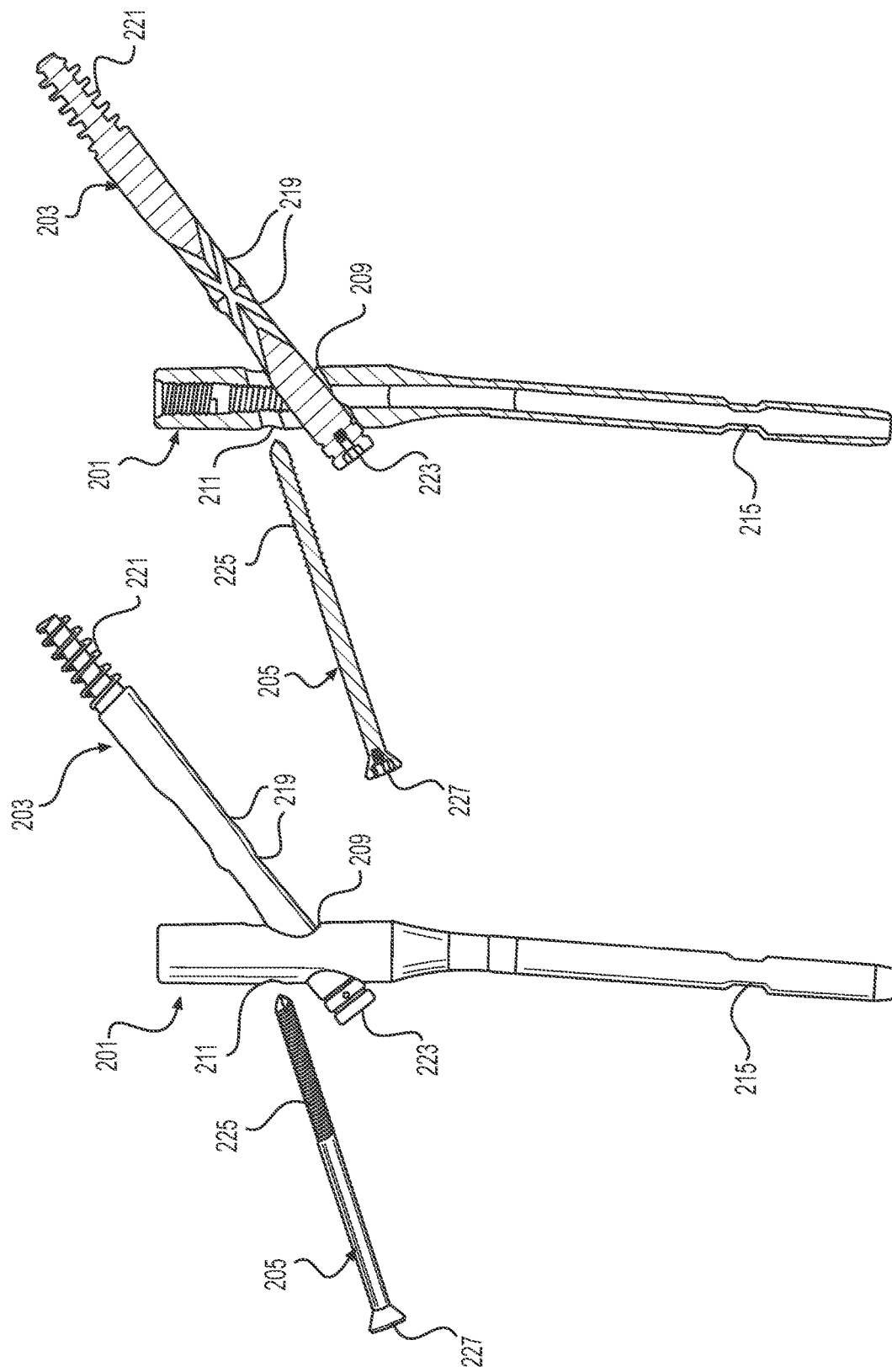
FIGS. 6A-6D illustrate various views of a second fixation device and the intramedullary nail with the first fixation device inserted therein.
Figure 6D:
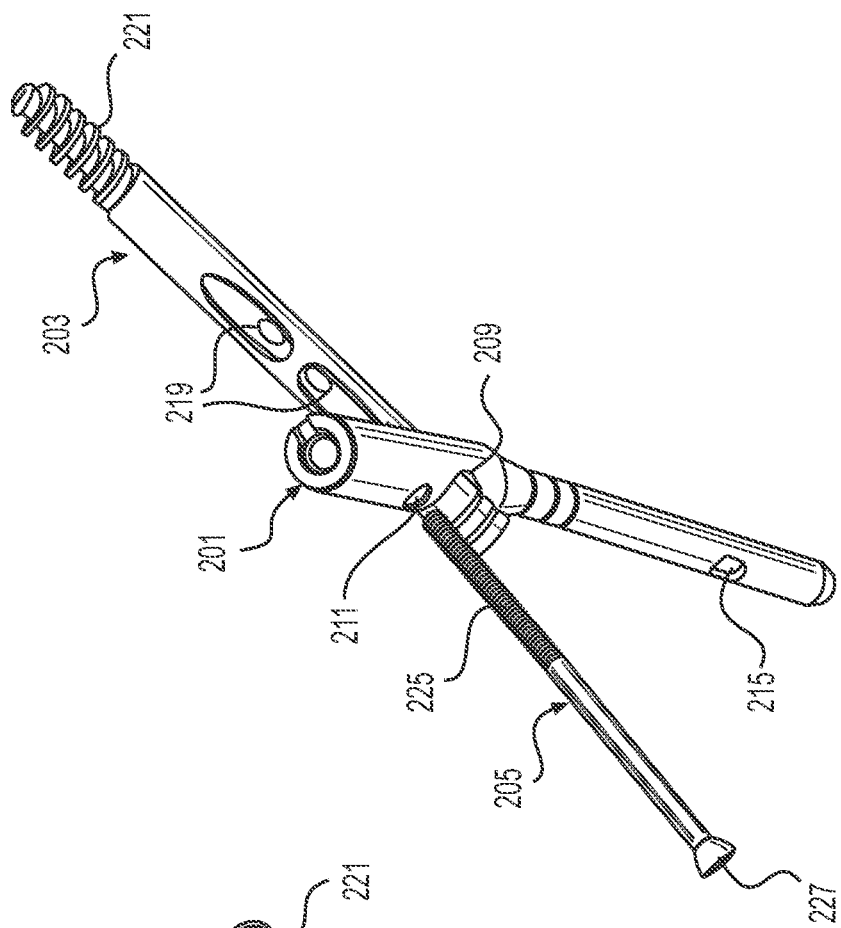
Figure 6C:
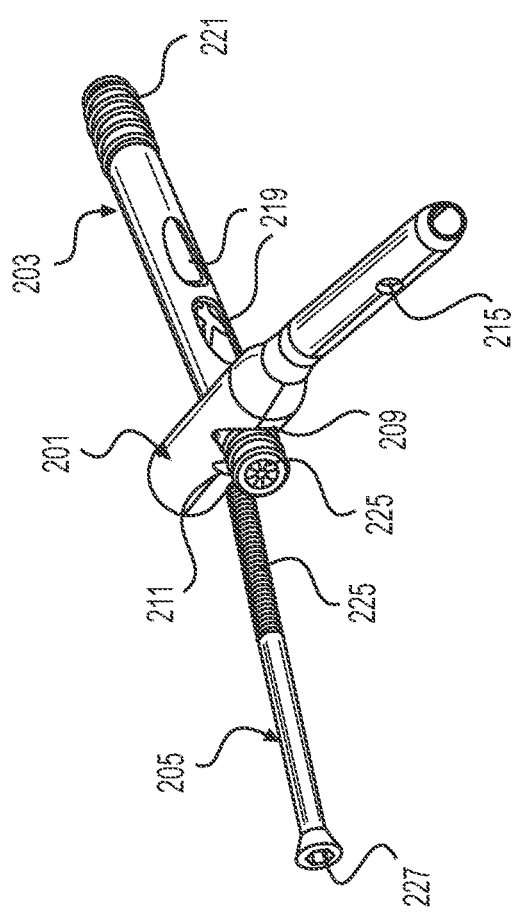
Figure 7D:
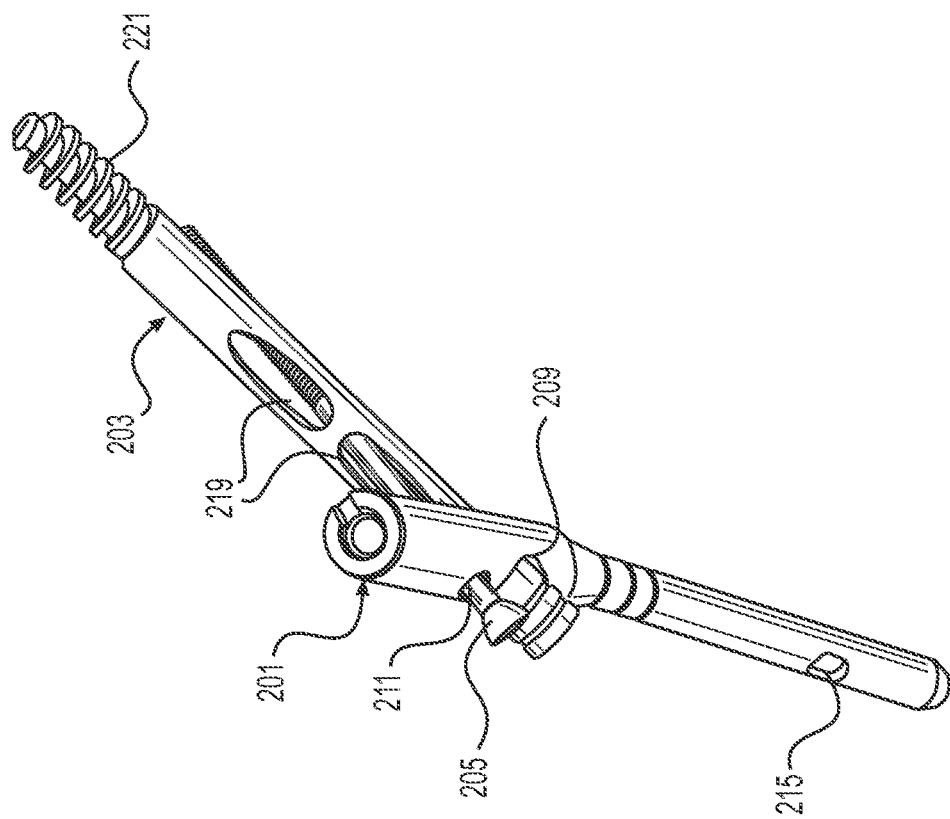
Figure 7C:
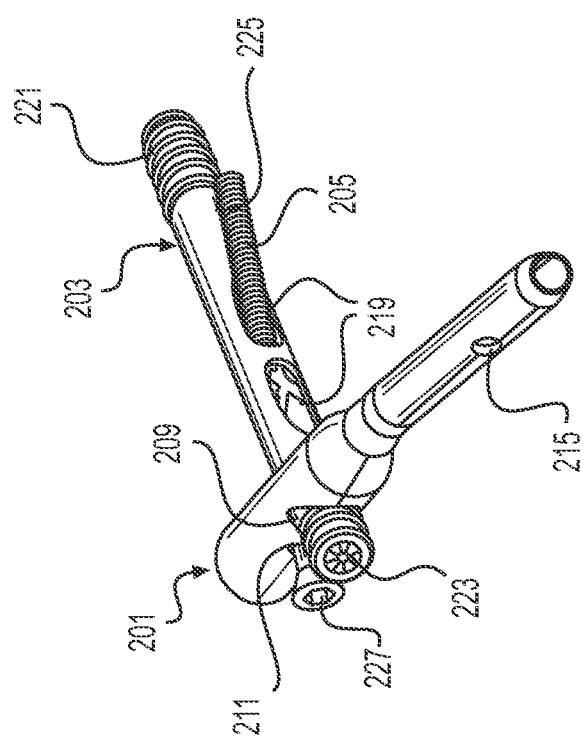
Figures 11A, 11B, 11C:
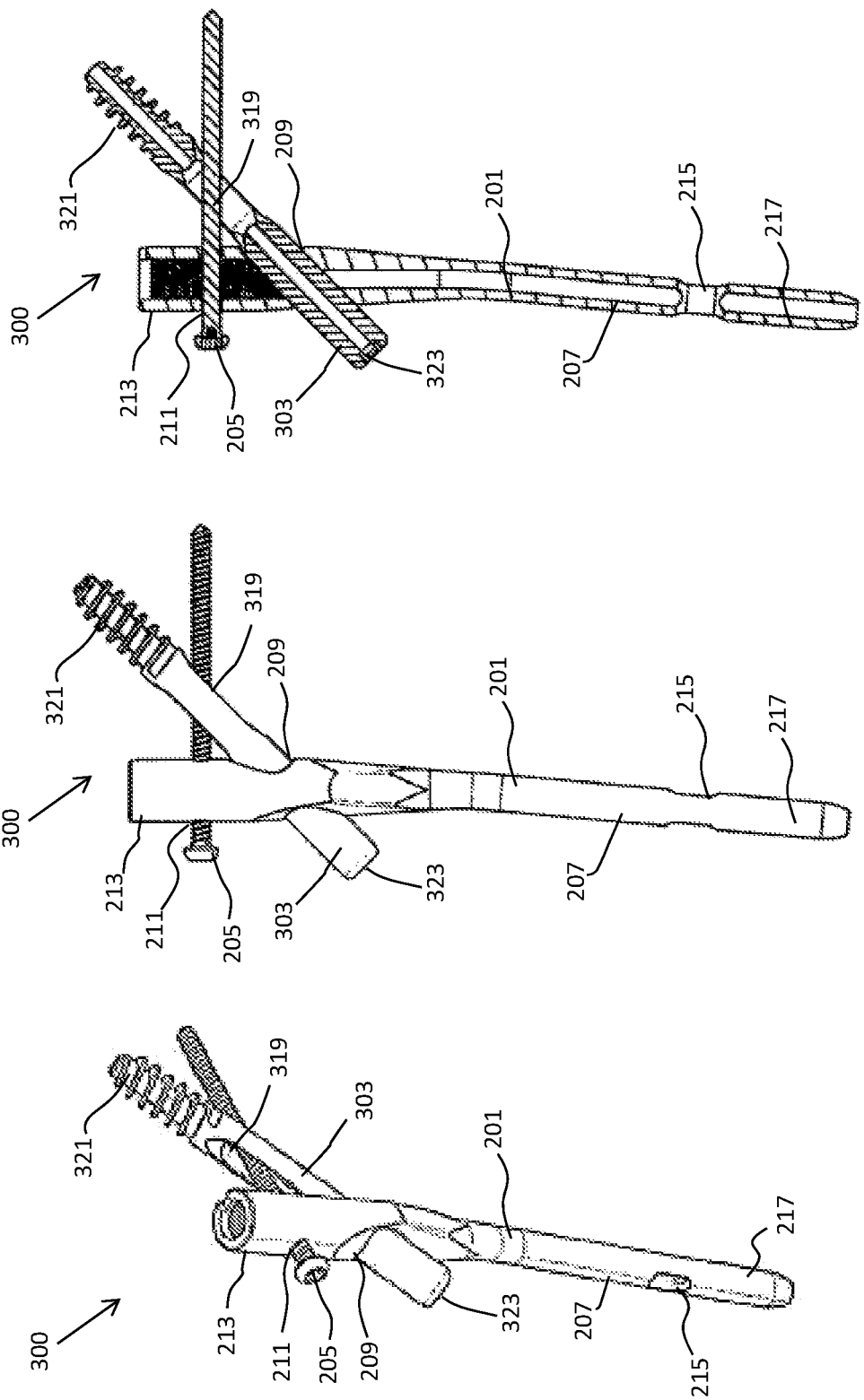
FIGS. 11A-11C illustrate various views of a second fixation device inserted through the intramedullary nail and the first fixation device.

FIGS. 1A and 3F illustrate one example of an intramedullary nail 109, which may comprise a generally elongate body extending from a first, distal portion or end 110 to a second, proximal portion or end 111. The elongate body may be in the form of an elongate tubular rod configured to extend longitudinally within the intramedullary canal of a fractured bone. The elongate rod may be hollow or may be solid along its length. The elongate body may be substantially straight along a longitudinal axis of the nail 109 or may comprise one or more curves or bends to conform to the anatomical shape of the intramedullary canal. The cross-section of the nail 109, taken at a right angle to a central longitudinal axis of the intramedullary nail 109, may be circular, oval, elliptical, or of any other suitable cross-dimensional shape. The proximal portion 111 may have an enlarged diameter or head portion relative to the distal portion 110 of the nail 109. The enlarged head portion 111 may be sized and configured to be received in the greater trochanter region of the femur. The intramedullary nail 109 may be configured to be positioned in the proximal end of the femur for cephalomedullary fixation. It is envisioned, however, that the intramedullary nail 109 may be configured to be positioned through other approaches and locations (e.g., distal end) depending on the bone (e.g., femur, tibia) and type of fracture.

The distal end 110 may include one or more openings 125 configured to receive one or more bone anchors, fasteners, or distal fixation devices 147 that extend transversely through the distal end 110 of the intramedullary nail 109, and are thereby configured to secure the distal end 110 of the nail 109 within the canal. The distal fixation devices 147 may include a bone screw or anchor configured for distal locking of the nail 109. The distal fixation device 147 may include traditional polyaxial or fixed angle locking bone screws and anchors known in the art.

The proximal end 111 may also include one or more openings 123 configured to receive one or more bone anchors or fasteners 119 that extend transversely through the proximal end 111 of the intramedullary nail 109, and are thereby configured to secure the proximal end 111 of the nail 109 within the canal. The proximal fixation devices 119 may include a bone screw or anchor configured for proximal locking of the nail 109. The fixation device 119 may be a calcar screw or anchor configured to be aimed at a calcar region of the proximal femur, which may constitute the best quality bone in the region. The opening 123 and anchor 119 may be angled, for example, about 100-150°, 110-140°, or about 120-135° relative to the nail 119 to engage the calcar region of the bone. The calcar screw 119 may have an enlarged diameter relative to the distal screw 147. The proximal fixation device 119 may include traditional polyaxial or fixed angle calcar screws and anchors known in the art. The proximal end 111 may also include additional openings 123, for example, for one or more cross-locking devices (e.g., device 205 described in more detail below).

The intramedullary nail 109 and anchors 119, 147 may be comprised of any suitable biocompatible materials. The intramedullary nail 109 and anchors 119, 147 may be comprised of titanium, cobalt chrome, cobalt-chrome-molybdenum, stainless steel, tungsten carbide, carbon composite, plastic or polymer—such as polyetheretherketone (PEEK), polyethylene, ultra high molecular weight polyethylene (UHMWPE), resorbable polylactic acid (PLA), polyglycolic acid (PGA), combinations or alloys of such materials, or other appropriate biocompatible materials that have sufficient strength to secure and hold bone, while also having sufficient biocompatibility to be implanted into a body.

System for Intramedullary Nail Implantation

Figure 1B:
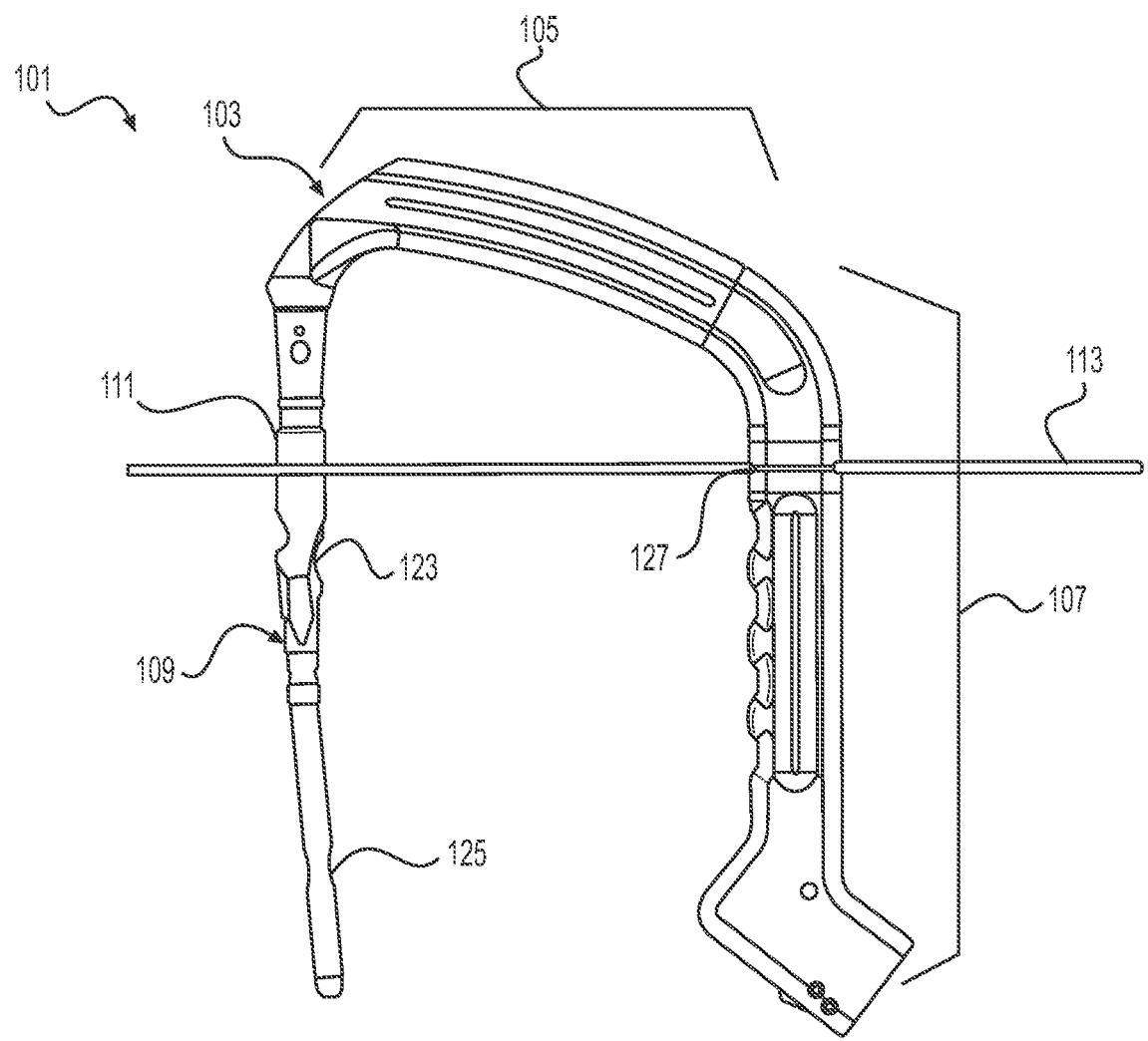

FIGS. 1A and 1B illustrate perspective and side views, respectively, of one embodiment of a system 101 for implanting an intramedullary nail 109. The system 101 includes an insertion tool 103 that has a coupling portion 105 and a handle portion 107. In some embodiments, the coupling portion 105 and the handle portion 107 can be separate parts that are removably joined together, while in other embodiments the coupling portion 105 and the handle portion 107 can be different regions of a single, integrally formed component. The coupling portion 105 releasably engages or couples to the proximal portion 111 of the nail 109. For example, the free end of the coupling portion 105 can be provided with a snap-fit design to temporarily retain a position of the intramedullary nail 109 prior to insertion of a fixation device 119 therethrough. However, those skilled in the art will understand that other coupling mechanisms may be employed.

The handle portion 107 may include one or more openings 127, 129 configured to receive one or more guide wires 113, 115. In one embodiment, the system 101 may include first and second guide wires 113, 115 as well as an optional guide sheath 117 through which the fixation device 119 may pass (e.g., the fixation device 119 can be inserted using the driver 121). As illustrated, the first and second guide wires 113, 115 may pass on opposing sides of both the nail 109 and the fixation device 119 (e.g. on posterior and anterior sides). Although the illustrated embodiment shows two guide wires, in other embodiments a single guide wire and corresponding guide wire hole may be used. In still other embodiments, three or more guide wires may be used. Additionally, the position and orientation of the guide wire holes can vary in different embodiments, for example being disposed more proximally or more distally along the insertion tool, etc.

As illustrated, the insertion tool 103 allows the user to place one or more guide wires 113, 115. In one embodiment, the guide wires 113, 155 are positioned both anterior and posterior to the nail 109. The guide wires 113, 115 may be positioned in this manner to prevent the distal fragments of the bone (e.g., distal fragments of the femoral head and neck) from rotating about the axis of the fixation device 119 when the fixation device 119 is advanced through the nail 109 and into the bone during the procedure. The handle portion 107 of the insertion tool 103 may include two guide wire receiving features such as holes 127, 129 on the opposing sides of the tool 103 that allow guide wires 113, 115 to pass through the respective holes. The guide wires 113, 115 are passed through the soft tissue and into the bone to help stabilize the insertion tool 103. In this configuration, the insertion tool 103 may not require any other instruments to guide the wires 113, 115 into the patient. The insertion tool 103 can achieve stability by resisting both rotational movement about the axis of the nail 109 as well as axial translation along the axis of the nail 109.

Figure 2A:
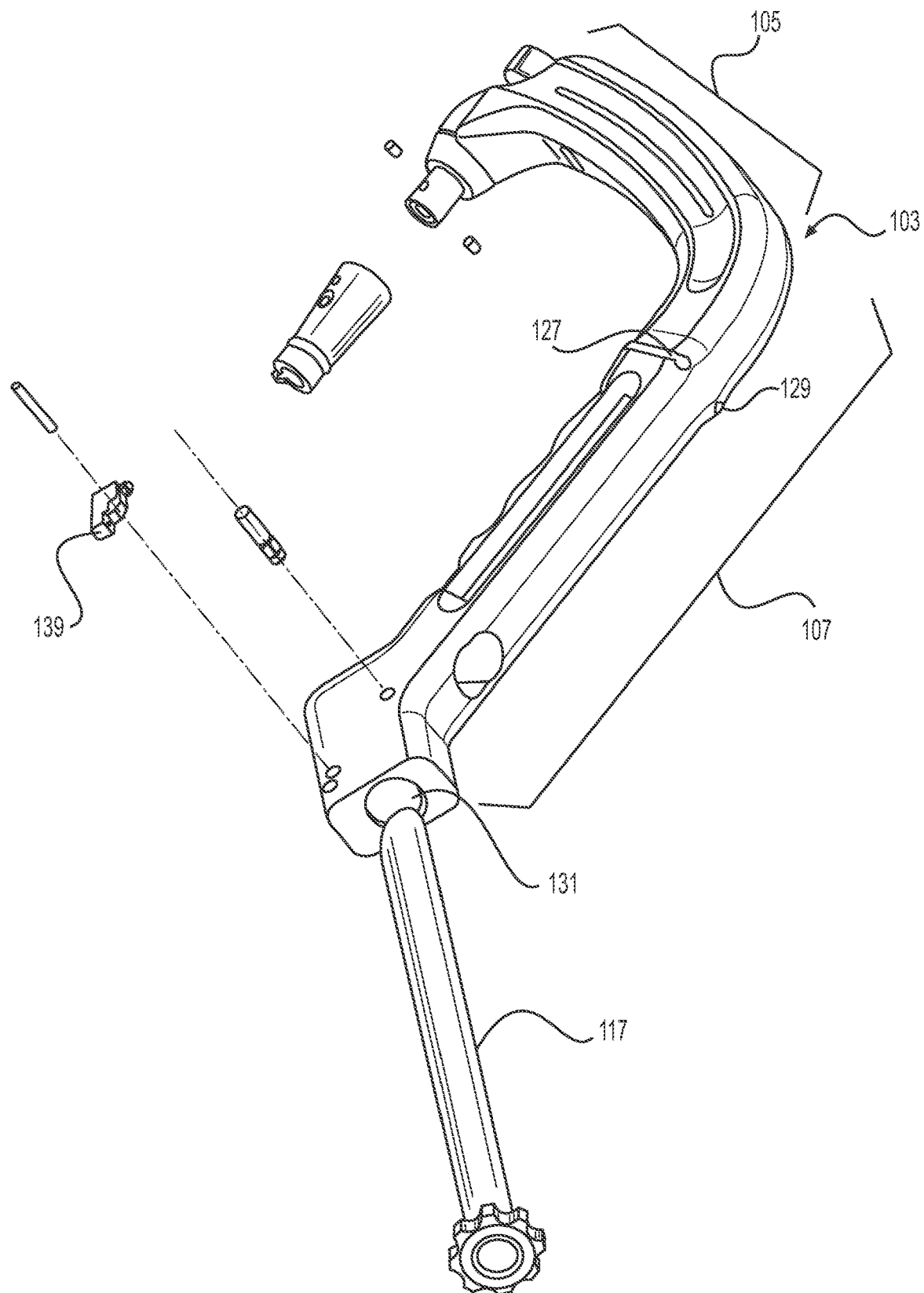
FIGS. 2A-2C illustrate various views of an insertion handle of the system shown in FIGS. 1A and 1B.
Figure 2B:
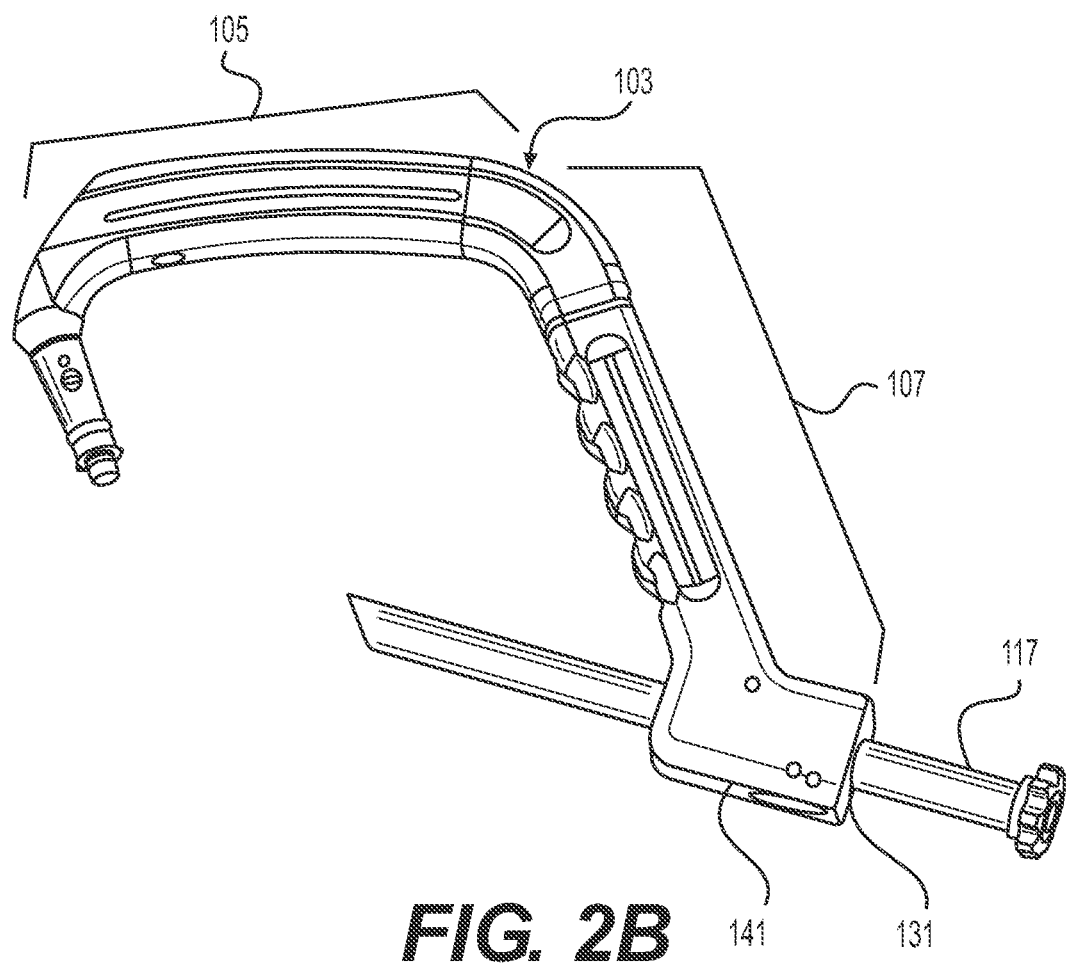
Figure 2C:
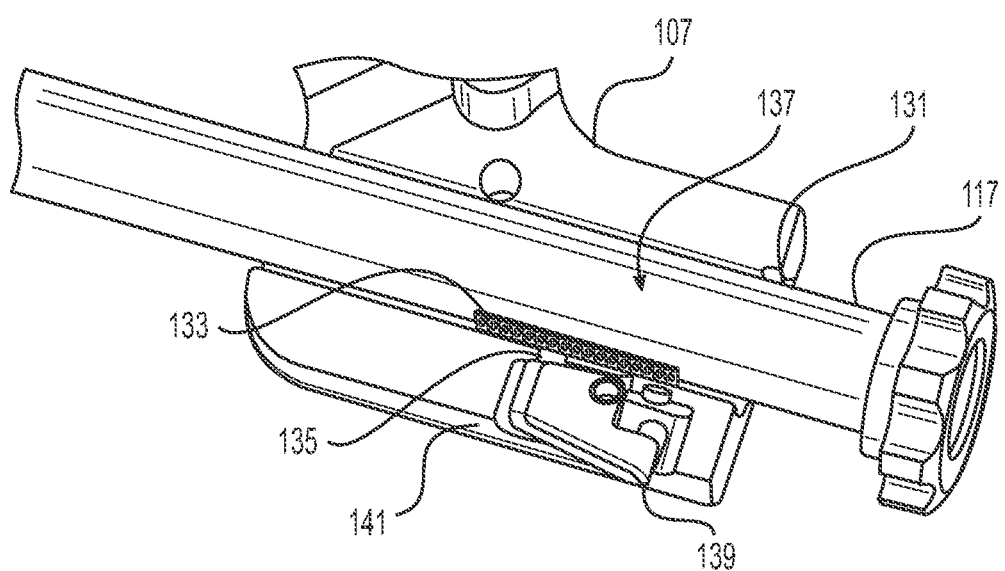

FIGS. 2A-2C illustrate various views of the insertion tool 103 of the system 101 shown in FIGS. 1A and 1B. In particular, FIG. 2A is a partially exploded perspective view of the insertion tool 103 adjacent to the guide sheath 117, FIG. 2B is a perspective view of the insertion tool 103 with the guide sheath 117 partially inserted therein, and FIG. 2C is an enlarged partial cross-sectional view of the engagement between the guide sheath 117 and the insertion tool 103.

The guide sheath 117 can be removably inserted through a guide sheath receiving feature such as a hole 131 formed in the handle portion 107 of the insertion tool 103. The guide sheath hole 131 defines an axis that intersects with a first aperture 123 in the nail 109. The guide sheath 117 can be positioned through the guide sheath hole 131 such that it substantially aligns with the first aperture 123 in the nail 109, which is configured to receive fixation device 119 aimed at the calcar region of the bone. The guide sheath 117 can include a first retention member 133 on an outer surface of the guide sheath 117. The first retention member 133 can include, for example, ridged teeth, protrusions, or other such surface configured to engage with a corresponding second retention member 135 disposed within the guide sheath hole 131. The second retention member 135 can likewise include one or more ridges or protrusions. Together the first and second retention members 133, 135 form a retention mechanism 137 that allows the guide sheath 117 to be ratcheted towards the intramedullary nail 109 while restricting movement of the guide sheath 117 away from the intramedullary nail. The retention release mechanism 139 can disengage the second retention member 135 from the first retention member 133 when pressed by a user. For example, the retention release mechanism 139 can be a button disposed on a lower surface 141 of the handle portion 107. Positioning this retention release mechanism 139 on the lower surface 141 of the insertion handle may prevent a user from accidentally releasing the guide sheath 117 while operating the device (e.g., while grasping the handle portion 107).

FIGS. 3A-3F illustrate one method of steps of implanting an intramedullary nail into a fractured femur 143. Referring first to FIG. 3A, a proximal end of the femur 143 can be accessed and the medullary cavity of the femur 143 can be reamed using a bone drill and reamer 145. Next, as shown in FIG. 3B, the intramedullary nail 109 is coupled to the insertion tool 103 and the intramedullary nail 109 is disposed within the reamed cavity of the femur 143. In FIG. 3C, when used, one or more of the first and second guide wires 113 and 115 may be inserted through the soft tissue, for example, along parallel trajectories on opposing sides of the nail 109. The guide wires 113, 115 can limit or prevent inadvertent rotation of distal fragments of the femur 143 after the nail 109 is in position. The proximal fixation device 119 (e.g., a lag screw or other suitable bone anchor) is also passed through the first aperture 123 in the nail 109 and into the head/neck region of the femur 143. In FIG. 3D, the guide wires 113, 115 are retracted and in FIG. 3E, the distal fixation device 147 can additionally be inserted through the distal aperture 125 in the nail 109. The distal device 147 can be positioned using the guide sheath 117, which is positioned through another opening in the handle portion 107, such that the sheath 1117 is aligned with the distal opening 125 in the nail 109. In FIG. 3F, the insertion tool 103 is disengaged from the nail 109, which is now secured in place via the proximal fixation device 119 and the distal fixation device 147. As shown, the nail 109 may extend along a portion of the length of femur 143. It is also contemplated, however, that the nail 109 may be of different sizes and shapes, for example, of longer lengths and/or different diameters to accommodate different anatomies and fractures.

Interlocking Fixation Devices for Intramedullary Nail Fixation

FIGS. 4A-4D illustrate another embodiment of an intramedullary nail 201, similar to intramedullary nail 109, with the addition of a cross-locking feature for proximal locking of the nail 201. Intramedullary nail 201 may include any of the features described above with respect to intramedullary nail 109. Intramedullary nail 201 may further include two interlocking proximal fixation devices 203, 205 (e.g., bone anchors, fasteners, or screws), for example, by providing converging and diverging purchase, along with bony fixation in the calcar of the femur 229, which is the strongest portion of the hip bone. Accordingly, the risk of failure due to cutout and/or rotation may be reduced.

FIGS. 4A-4D show side, side cross-sectional, and two perspective views, respectively, of the intramedullary nail 201 adjacent to a first fixation device 203. FIGS. 5A-5D illustrate side, side cross-sectional, and two perspective views, respectively, of the first, proximal fixation device 203 inserted through the intramedullary nail 201. FIGS. 6A-6D illustrate side, side cross-sectional, and two perspective views, respectively, of the system with a second, cross-locking fixation device 205 adjacent to the intramedullary nail 201 with the first fixation device 203 inserted therein. FIGS. 7A-7D illustrate side, side cross-sectional, and two perspective views, respectively, of the system with the second fixation device 205 inserted through both the intramedullary nail 201 and the first fixation device 203, thereby creating a cross-locking feature for proximal locking of the nail 201.

Referring to FIGS. 4A-8C together, the intramedullary nail 201 is configured to receive both the first and second fixation devices 203 and 205 therein. The intramedullary nail 201 includes an elongated body 207 having first and second apertures 209 and 211 formed therethrough in a proximal region 213, as well as a third aperture 215 formed in a distal region 217. The first aperture 209 can be sized and configured to receive the first fixation device 203 therethrough and the second aperture 211 can be sized and configured to receive the second fixation device 205 therethrough.

The first fixation device 203, may be the same or similar to the proximal fixation device 119, described herein, and may include a bone screw or anchor configured for proximal locking of the nail 201. For example, the first fixation device 203 may be a hip screw or anchor configured to be aimed at a head region of the proximal femur. The anchor 203 may have a threaded portion at its distal tip and a non-threaded portion along a substantial length of the screw 203. The anchor 203 may include traditional polyaxial or fixed angle screws and anchors known in the art.

The second fixation device 205 may also include a bone screw or anchor configured for proximal locking of the nail 201. This bone anchor or screw 205 may be substantially smaller in length and diameter relative to the calcar screw 203. The bone anchor or screw 205 is substantially sized and configured to be positioned through second opening 211 in the proximal end of the nail 201 and into a channel 219 in the first fixation device 203. Thus, the second device 205 is configured to interlock with the first fixation device 203, for example, for enhanced purchase and bony fixation to the bone. The second fixation device 205 may be positioned to engage at or near the calcar region of bone. Although shown with the second fixation device 205 positioned above the first fixation device 203 and angled downwardly into contact with the first fixation device 203, it is also envisioned that these relative positons may be reversed or the fixation devices 203, 205 may otherwise be angled with respect to one another in order to interlock the devices 203, 205 with one another. The second fixation device 205 may be configured to pass through a slot or channel 219 formed in the first fixation device 203. This interlocking feature of the first and second fixation devices 203, 205 can prevent cutout and rotation by providing converging and diverging purchase. In the case of a femur, this can also provide bony fixation in the calcar. The elongated slot 219 in the first fixation device 203 allows for controlled collapse, which leverages the natural compression between fragments from weight bearing or ligamentotaxis. Limited collapse is controlled by the length of the slot 219 to prevent the uncontrolled and excessive shortening of the femoral neck. The first fixation device 203 may include distal threads 221 and a proximal drive interface 223 configured to engage with a driver (not shown). The second fixation device 205 may have a narrower diameter than the first fixation device 203 such that the second fixation device 205 can pass through the slot 219 in the first fixation device 203. The second fixation device 205 may also include distal threads 225 and a proximal drive interface 227 configured to engage with a driver (not shown).

The slot 219 can be disposed in the mid-shaft of the first fixation device 203 and may be sized and configured to allow the second fixation device 205 to pass therethrough. The slot 219 may be longer than necessary to allow translation of the first fixation device 203 after the second fixation device 205 is in place. The slot 219 may be strong enough to prevent rotation of the first fixation device 203 after the second fixation device 205 is in position. The slot 219 may have beveled proximal and distal edges to maximize material in the first fixation device 203 while allowing proximal and distal clearance of the second fixation device 205. The slot 219, in the first fixation device 203, may be symmetric to allow positioning of the second fixation device 205 in 180° increments, for example.

In at least one embodiment, a locking device 230, such as a set screw or washer, may be used to lock the first and/or the second fixation devices 203, 205 into position. As best seen in FIG. 7B, the locking device 230 may be threaded through a hollow interior portion of the nail 201. The locking device 230 may have external threads, which are sized and configured to correspond to mating internal threads along the hollow interior portion of the nail 201. As the locking device 230 is threaded downwardly and comes into contact with the first or second fixation devices 203, 205, the respective fixation device 203, 205 is locked into position relative to the nail 201. In some embodiments, the interlocking fixation devices 203, 205 can be used selectively. For example, the threaded locking device 230 may be threaded to engage the second fixation device 205; alternatively, the threaded locking device 230 may be threaded further down to lock the first fixation device 203, for example, if the second fixation device 205 is not used. This allows users the choice of a traditional or interlocking construct intraoperatively.

An insertion tool 103 for implanting the system including the nail 201 and the interlocking first and second fixation devices 203 and 205 can be substantially similar to the system 101 described above with respect to FIGS. 1A-2C, except that an additional guide sheath hole may be formed in the handle portion 107 to accommodate a guide sheath along an appropriate trajectory to insert the second fixation device 205 through the second aperture 211 in the nail 201 and into engagement with the first fixation device 203.

FIGS. 8A-8C illustrate one method of steps of implanting an intramedullary nail 201 with interlocking fixation devices 203, 205 into a fractured femur 229. Referring first to FIG. 8A, the nail 201 has been inserted into a reamed medullary cavity of the femur 229 and the first fixation device 203 has been inserted through the first aperture 209 in the nail 201, similar to the technique described above with respect to FIGS. 3A-3D. Referring to FIG. 8B, a distal fixation device 231 can be inserted through the third aperture 215 in the nail 201, similar to the technique described above with respect to FIG. 3E. Referring to FIG. 8C, the second fixation device 205 is inserted through the second aperture 211 in the nail 201 and through the slot 219 in the first fixation device 203. As noted, these intersecting first and second fixation devices 203, 205 provide additional purchase in the head and neck region of the femur 229, and in particular the second fixation device 205 can provide bony fixation in the calcar. Accordingly, the interlocking first and second fixation devices 203, 205 can provide for improved stability and protection against common modes of intramedullary nail implant failure.

Turning now to FIGS. 9A-12E, cross-locking system 300 is shown according to yet another embodiment. This embodiment is similar to the cross-locking embodiment shown in FIGS. 4A-7D except the two crossing slots 219 are replaced with a single elongated slot 319 in the first fixation device 303. The intramedullary nail 201 and second fixation device 205 are the same or similar to those described herein.

With reference to FIGS. 9A-9C, an alternative version of the cross-locking system 300 is shown. The intramedullary nail 201 and the first fixation device 303 are depicted in a perspective view, side view, and cross-sectional view, respectively. The first fixation device 303 may be in the form of a bone anchor configured for proximal locking of the nail 201. For example, the first fixation device 303 may be a hip anchor, for example, configured to be aimed at a neck region of a long bone. The first fixation device 303 may extend from a proximal end having a proximal drive feature 323, such as an opening for receiving a driver, to a distal end including a threaded portion 321. A non-threaded portion may extend from the proximal end along a substantial length of the anchor 303. The anchor 303 may include features of traditional polyaxial or fixed angle screws and anchors known in the art.

Figure 12A:
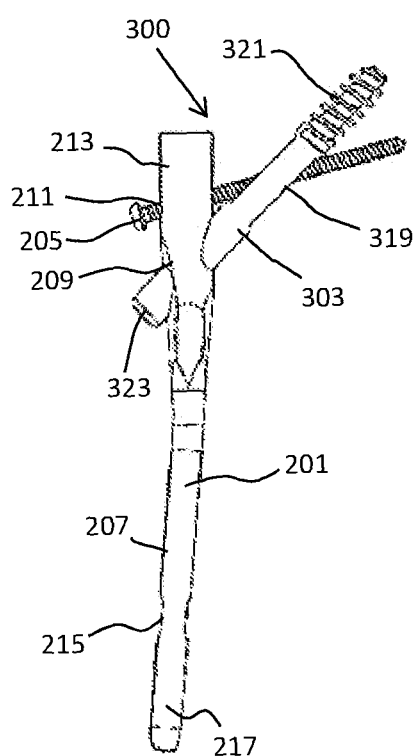
FIGS. 12A-12E illustrate various views of the second fixation device inserted through the intramedullary nail and the first fixation device.
Figure 12B:
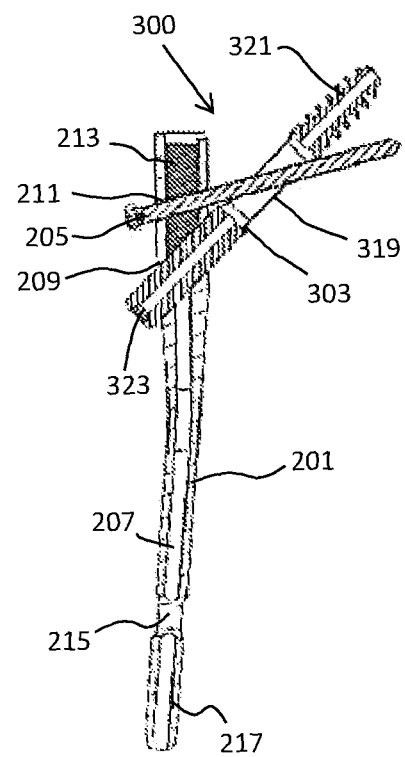
Figure 12C:
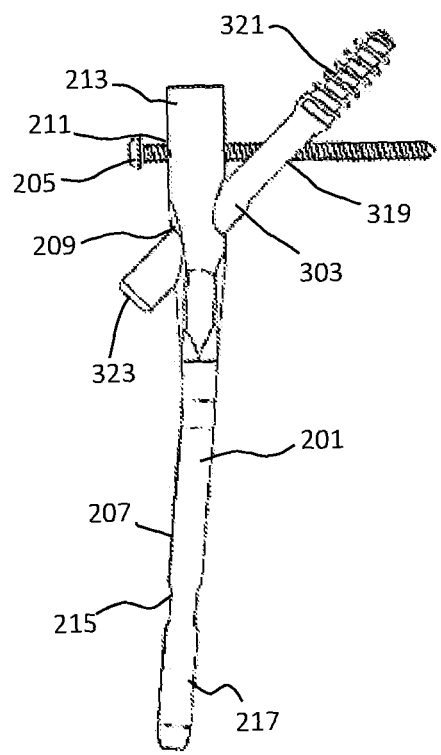
Figure 12D:
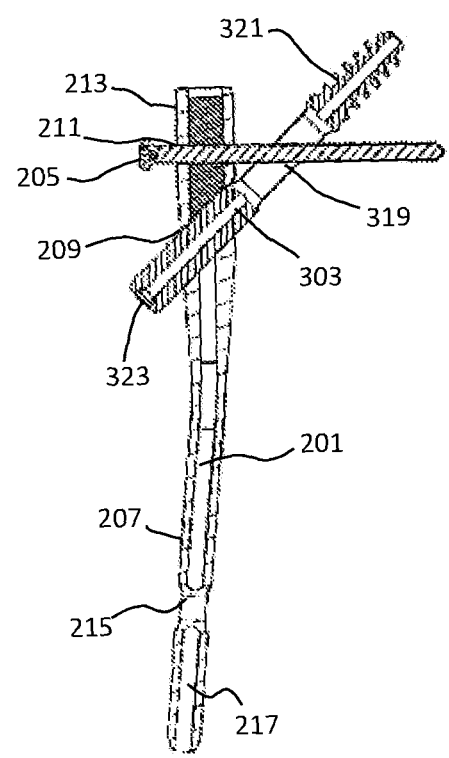
Figure 12E:
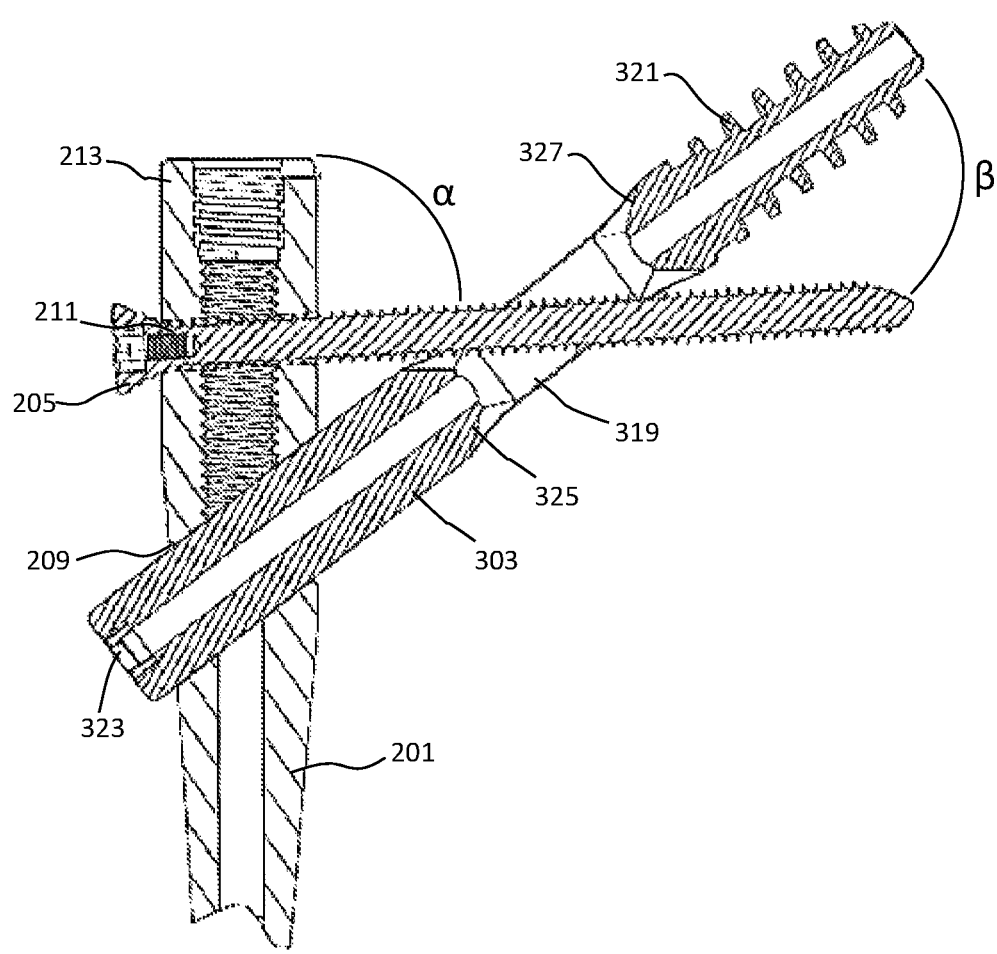

The first fixation device 303 includes an elongate opening, slot, or channel 319 extending therethrough. The channel 319 may be disposed in the mid-shaft of the first fixation device 303, for example, along the non-threaded portion. As best seen in FIG. 12E, the elongated slot 319 may extend from a proximal end 325 to a distal end 327. The proximal and distal ends 325, 327 of the elongate slot 319 may be straight, rounded, beveled, angled, or the like. In the embodiment shown, the proximal and distal ends 325, 327 may each transition from a first angled portion to a curved central portion to a second angled portion.

The second fixation device 205 is configured to interlock with the first fixation device 303. The second fixation device 205 is sized and configured to be positioned through the second opening 211 in the proximal end of the nail 201 and into the channel 319 in the first fixation device 303. The second fixation device 205 is configured to pass through the slot or channel 319 formed in the first fixation device 303 to provide for an interlocking feature of the first and second fixation devices 303, 205. The elongated slot 319 in the first fixation device 303 may provide for controlled or limited collapse of the first and second fixation devices 303, 2015, which may be controlled by the length of the slot 319.

The second fixation device 205 may be positioned at an angle α relative to the intramedullary nail 201. The angle α may extend between a longitudinal axis of the intramedullary nail 201 and a longitudinal axis of the second fixation device 205. The angle α may range from about 0-130°, about 0-90°, about 70-90°, or about 80-90°. The opening or aperture 211 in the intramedullary nail 201 may be angled, beveled, or provided with enough clearance to allow for variable angles of angle α. As shown in the side view and cross-sectional views of FIGS. 12A and 12B, respectively, second fixation device 205 may be at angle α of less than 90°. In FIGS. 12C and 12D, the second fixation device 205 is shown at angle α of about 90°.

The second fixation device 205 is also positioned at an angle β relative to the first fixation device 303. The angle β may extend between a longitudinal axis of the first fixation device 303 and a longitudinal axis of the second fixation device 205 relative to their distal most tips. The angle β may range from about 0-120°, about 0-90°, about 0-65°, about 0-45°, or about 25-65°. The opening or aperture 209 in the intramedullary nail 201 may be angled, beveled, or provided with enough clearance to allow for variable angles of angle β.

The channel or slot 319 may be sized substantially larger than an outer diameter of the second fixation device 205, for example, more than double, triple, or quadruple the outer diameter of the second fixation device 205. The enlarged slot 319 is sized to allow the second fixation device 205 to pass therethrough and translate along the length of the slot 319. The elongated slot 319 may allow for translation of the first fixation device 303 and/or the second fixation device 205 after the first and second fixation devices 303, 205 are implanted in bone. After implantation, the second fixation device 205 may reside within the slot 319 without contacting either of the proximal or distal ends 325, 327. The second fixation device 205 may be permitted to translate in the slot 319 until the second fixation device 205 contacts one of the first proximal or distal ends 325, 327, for example, one of the angled portions of the end 325, 327.

The cross-locking system 300 may address one or more of the major failure modes for hip fixation: axial cutout, cephalad cutout, fragment rotation, and nonunion. For example, the intersecting first and second fixation devices 303, 205 may provide for enhanced purchase in the head and neck region of the elongate bone. The overall system 300 can provide for improved stability and protection against common modes of implant failure.

CONCLUSION

The above detailed descriptions of embodiments of the technology are not intended to be exhaustive or to limit the technology to the precise form disclosed above. Although specific embodiments of, and examples for, the technology are described above for illustrative purposes, various equivalent modifications are possible within the scope of the technology, as those skilled in the relevant art will recognize. For example, while steps are presented in a given order, alternative embodiments may perform steps in a different order. The various embodiments described herein may also be combined to provide further embodiments.

From the foregoing, it will be appreciated that specific embodiments of the invention have been described herein for purposes of illustration, but well-known structures and functions have not been shown or described in detail to avoid unnecessarily obscuring the description of the embodiments of the technology. Where the context permits, singular or plural terms may also include the plural or singular term, respectively.

Moreover, unless the word "or" is expressly limited to mean only a single item exclusive from the other items in reference to a list of two or more items, then the use of "or" in such a list is to be interpreted as including (a) any single item in the list, (b) all of the items in the list, or (c) any combination of the items in the list. Additionally, the term "comprising" is used throughout to mean including at least the recited feature(s) such that any greater number of the same feature and/or additional types of other features are not precluded. It will also be appreciated that specific embodiments have been described herein for purposes of illustration, but that various modifications may be made without deviating from the technology. Further, while advantages associated with certain embodiments of the technology have been described in the context of those embodiments, other embodiments may also exhibit such advantages, and not all embodiments need necessarily exhibit such advantages to fall within the scope of the technology. Accordingly, the disclosure and associated technology can encompass other embodiments not expressly shown or described herein.

What is claimed is:

1. An implant, comprising:
  an intramedullary nail having:
  an elongate body extending from a proximal portion to a distal portion, a portion of the elongate body extending along a first axis;
  a first aperture formed in the proximal portion, the first aperture defining a second axis transverse to the first axis; and
  a second aperture formed in the proximal portion, the second aperture being spaced apart from the first aperture, the second aperture defining a third axis transverse to the first axis, the third axis intersecting with the second axis at a point spaced apart from the body;
  an anchor having a longitudinal axis and positionable through the first aperture in the nail, the anchor having an elongate aperture extending through the anchor, the elongate aperture having a first opening and a second opening and a passageway extending from the first opening to the second opening; and
  a fastener positionable through the second aperture in the nail, and the fastener positionable through the elongate aperture in the anchor such that the fastener extends through the first opening and the second opening,
  wherein the anchor extends from a proximal end portion to a distal end portion, and the anchor has a threaded distal portion.

2. The implant of claim 1, wherein the elongate aperture is positioned centrally between the distal end portion and the proximal end portion.

3. The implant of claim 1, wherein the fastener is threaded along its length.

4. The implant of claim 1, wherein the elongate aperture in the anchor has a length greater than a diameter of the fastener and is sized to allow translation of the anchor after the fastener has been passed through the elongate aperture.

5. The implant of claim 1, wherein an angle between the anchor and the fastener is up to 120° between distal tips of the anchor and the fastener.

6. The implant of claim 1, wherein the elongate aperture in the anchor comprises beveled proximal and distal edges.

7. The implant of claim 1, wherein the intramedullary nail further comprises a third aperture in the distal portion of the nail.

8. The implant of claim 7, wherein a distal fastener is positionable through the third aperture to thereby secure the distal portion of the nail.

9. An implant comprising:
an intramedullary nail having:
- an elongate body having a first axis and extending from a proximal portion to a distal portion;
- a first aperture formed in the proximal portion of the elongate body, the first aperture defining a second axis transverse to the first axis;
- a second aperture formed in the elongate body, the second aperture being spaced apart from the first aperture;

a bone anchor having a linear longitudinal axis extending from a proximal portion to a distal portion of the bone anchor and an elongate opening extending through the bone anchor from a first side portion to a second side portion, the bone anchor positionable through the first aperture in the elongate body such that the elongate opening is positioned outside the intramedullary nail, and a screw, the screw positionable through second aperture in the elongate body and through the elongate opening in the bone anchor such that a distal tip of the screw extends beyond the second side portion of the bone anchor.

10. The implant of claim 9, wherein the second aperture is formed in the proximal portion of the intramedullary nail.

11. The implant of claim 10, wherein the second aperture defines a third axis transverse to the first axis, the third axis intersects with the second axis at a point spaced apart from the elongate body.

12. The implant of claim 10, wherein the screw is a calcar screw.

13. The implant of claim 12, wherein the calcar screw is threaded along its length.

14. The implant of claim 12, wherein the elongate opening in the bone anchor has a length greater than a diameter of the calcar screw and is sized to allow translation of the bone anchor and calcar screw after the calcar screw has been passed through the elongate opening slot.

15. The implant of claim 9, wherein the elongate opening extends from a proximal edge to a distal edge, and the proximal and distal edges are beveled.

16. The implant of claim 9, further comprising a third aperture in the distal portion of the nail.

17. The implant of claim 16, wherein a distal fastener is positionable through the third aperture for distal locking of the intramedullary nail.

* * * * *